(12) United States Patent
McBride et al.

(10) Patent No.: US 6,887,241 B1
(45) Date of Patent: May 3, 2005

(54) ADJUSTABLE TRANSVERSE CONNECTOR WITH CAM ACTIVATED ENGAGERS

(75) Inventors: G. Grady McBride, Winter Park, FL (US); Robert J. Jones, Austin, TX (US); Scott D. Koysh, Lago Vista, TX (US)

(73) Assignee: Spinal Concepts, Inc., Austin, TX (US)

( * ) Notice: Subject to any disclaimer, the term of this patent is extended or adjusted under 35 U.S.C. 154(b) by 569 days.

(21) Appl. No.: 09/680,756

(22) Filed: Oct. 6, 2000

(51) Int. Cl.⁷ .............................................. A61B 17/56
(52) U.S. Cl. ...................................................... 606/61
(58) Field of Search .............................. 606/60, 61, 54

(56) References Cited

U.S. PATENT DOCUMENTS

| | | |
|---|---|---|
| 1,789,060 A | 1/1931 | Weisenbach |
| 3,565,066 A | 2/1971 | Roaf |
| 3,693,616 A | 9/1972 | Roaf et al. |
| 4,085,744 A | 4/1978 | Lewis et al. |
| 4,112,935 A | 9/1978 | Latypov et al. |
| 4,190,222 A | 2/1980 | Appleton et al. |
| 4,269,178 A | 5/1981 | Keene |
| 4,274,401 A | 6/1981 | Miskew |
| 4,361,141 A | 11/1982 | Tanner |
| 4,361,144 A | 11/1982 | Slatis et al. |
| 4,369,770 A | 1/1983 | Bacal et al. |
| 4,411,259 A | 10/1983 | Drummond |
| 4,433,677 A | 2/1984 | Ulrich et al. |
| 4,448,191 A | 5/1984 | Rodnyansky et al. |
| 4,611,581 A | 9/1986 | Steffee |
| 4,611,582 A | 9/1986 | Duff |
| 4,648,388 A | 3/1987 | Steffee |
| 4,743,260 A | 5/1988 | Burton |
| 4,773,402 A | 9/1988 | Asher et al. |
| 4,854,304 A | 8/1989 | Zielke |

(Continued)

FOREIGN PATENT DOCUMENTS

| | | |
|---|---|---|
| DE | 19826380 | 12/1999 |
| EP | 0599640 | 6/1994 |
| EP | 0811357 | 12/1997 |
| EP | 0956829 | 11/1999 |
| WO | 97/38640 | 10/1997 |
| WO | 9904718 | 2/1999 |
| WO | 9965415 | 12/1999 |
| WO | 0019923 | 4/2000 |

OTHER PUBLICATIONS

Photocopy of Surgical Dynamics, Inc. Transverse Connector (Photocopy made before Oct., 2000).
International Search Report for International application No. PCT/US 01/31016, mailed on May 2, 2002.

Primary Examiner—David O. Reip
Assistant Examiner—D. Jacob Davis
(74) Attorney, Agent, or Firm—Beth A. Vrioni

(57) ABSTRACT

A transverse connector may be attached to rods of an orthopedic stabilization system. The rods of the stabilization system may be non-parallel and skewed in orientation relative to each other. The transverse connector may include two members that are joined together by a fastener. The transverse connector may be adjustable in three separate ways to allow the transverse connector to attach to the rods. The length of the transverse connector may be adjustable. The rod openings of the transverse connector may be partially rotatable about a longitudinal axis of the transverse connector. Also, a first member may be angled towards a second member so that the transverse connector can be attached to rods that are diverging. The transverse connector may include cam locks that securely attach the transverse connector to the rods. Rotating a cam locks may extend a rod engager into a rod opening. The rod engager may be a portion of the cam lock. The extension of the rod engager into a rod opening may push a rod against a body of the transverse connector to form a frictional engagement between the transverse connector, the rod, and the rod engager.

18 Claims, 13 Drawing Sheets

U.S. PATENT DOCUMENTS

| | | |
|---|---|---|
| 4,950,269 A | 8/1990 | Gaines, Jr. |
| 4,987,892 A | 1/1991 | Krag et al. |
| 5,005,562 A | 4/1991 | Cotrel |
| 5,024,213 A | 6/1991 | Asher et al. |
| 5,053,034 A | 10/1991 | Olerud |
| 5,084,049 A | 1/1992 | Asher et al. |
| 5,108,395 A | 4/1992 | Laurain |
| 5,122,131 A | 6/1992 | Tsou |
| 5,147,360 A | 9/1992 | Dubousset |
| 5,154,718 A | 10/1992 | Cozad et al. |
| 5,171,279 A | 12/1992 | Mathews |
| 5,176,678 A | 1/1993 | Tsou |
| 5,181,917 A | 1/1993 | Rogozinski |
| 5,209,752 A | 5/1993 | Ashman et al. |
| 5,246,442 A | 9/1993 | Ashman et al. |
| 5,257,994 A | 11/1993 | Lin |
| 5,261,909 A | 11/1993 | Sutterlin et al. |
| 5,282,801 A | 2/1994 | Sherman |
| 5,312,405 A | 5/1994 | Korotko et al. |
| 5,334,203 A | 8/1994 | Wagner |
| 5,342,361 A | 8/1994 | Yuan et al. |
| 5,344,422 A | 9/1994 | Frigg |
| 5,374,267 A | 12/1994 | Siegal |
| 5,413,602 A | 5/1995 | Metz-Stavenhagen |
| 5,437,669 A | 8/1995 | Yuan et al. |
| 5,439,463 A | 8/1995 | Lin |
| 5,498,263 A | 3/1996 | DiNello et al. |
| 5,549,607 A | 8/1996 | Olson et al. |
| 5,569,246 A | 10/1996 | Ojima et al. |
| 5,611,800 A | 3/1997 | Davis et al. |
| 5,624,441 A | 4/1997 | Sherman et al. |
| 5,667,507 A | 9/1997 | Corin et al. |
| 5,688,272 A | 11/1997 | Montague et al. |
| 5,688,275 A | 11/1997 | Koros et al. |
| 5,709,684 A | 1/1998 | Errico et al. |
| 5,752,955 A | 5/1998 | Errico |
| 5,785,713 A | 7/1998 | Jobe |
| 5,947,965 A | 9/1999 | Bryan |
| 5,947,966 A | 9/1999 | Drewry et al. |
| 5,980,521 A | 11/1999 | Montague et al. |
| 6,132,430 A | 10/2000 | Wagner |
| 6,283,967 B1 * | 9/2001 | Troxell et al. .............. 606/61 |
| 6,306,137 B2 * | 10/2001 | Troxell .................. 606/61 |
| 6,331,179 B1 * | 12/2001 | Freid et al. ................ 606/61 |
| 6,562,038 B1 * | 5/2003 | Morrison .................. 606/61 |
| 2003/0114853 A1 * | 6/2003 | Burgess et al. ............ 606/61 |

* cited by examiner

ADJUSTABLE TRANSVERSE CONNECTOR WITH CAM ACTIVATED ENGAGERS

BACKGROUND OF THE INVENTION

1. Field of the Invention

The present invention generally relates to bone stabilization systems, and more particularly to a transverse connector for connecting adjacent rods of orthopedic stabilization systems. The transverse connector, or cross-link, may connect together adjacent spinal rods of a spinal stabilization system.

2. Description of Related Art

Bone disorders, degenerative conditions, or trauma may result in a need to stabilize a bone or bones of a patient with an orthopedic stabilization system. For example, disease or trauma may result in the need to stabilize the spine of a patient. A variety of systems may be used to stabilize a spine. A spinal stabilization system may generally be classified as an anterior, lateral, or posterior system according to a position of the system relative to the spine. Posterior stabilization systems often include pairs of vertically aligned rods for stabilizing both short and long segments of a spine.

An orthopedic stabilization system may include a pair of rods that are coupled to a bone or bones. For example, a posterior spinal stabilization system may include a pair of bendable rods that are contoured and longitudinally disposed adjacent to vertebral bodies of a spine. A pair of rods of an orthopedic stabilization system may be coupled to a bone or bones by fixation elements. The fixation elements may include, but are not limited to, hooks and bone screw connectors.

Rods of an orthopedic stabilization system may be oriented so that the rods are substantially parallel to each other. Alternately, rods of an orthopedic stabilization system may be oriented so that the rods are skewed relative to each other. In a skewed orientation, the rods may be oriented towards each other so that a horizontal distance between the rods is not constant. In other words, the rods may not be horizontally parallel to each other. FIG. 1 shows a top view of a pair of rods 28 that are not horizontally parallel. Also, the rods 28 may be oriented so that a vertical distance between the rods is not constant. In other words, the rods 28 may not be vertically parallel to each other. FIG. 2 shows a pair of rods that are not vertically parallel.

Transverse connectors may be attached to connect adjacent rods of an orthopedic stabilization system together. Transverse connectors may provide rigidity to a stabilization system. Transverse connectors may also inhibit rod movement. Stresses may act to return a stabilized bone system to a deformed position. For example, stresses on a spine and on a spinal stabilization system often operate to return a corrected spine to a deformed position. Transverse connectors may inhibit rod movement of the spinal stabilization system during a post-operative period so that the spine remains in a corrected position.

Many transverse connectors have been developed that link adjacent rods together. U.S. patents and patent application Ser. No. 09/093,756 to Wagner et al.; U.S. Pat. No. 5,980,521 to Montague et al.; U.S. Pat. No. 5,947,966 to Drewry et al.; U.S. Pat. No. 5,752,955 to Errico et al.; U.S. Pat. No. 5,709,684 to Errico et al.; and U.S. Pat. No. 5,667,507 to Errico et al., describe transverse connectors. Each of these patents and patent applications are incorporated by reference as if fully set forth herein. Many transverse connectors present one or more problems for a surgical team that installs the transverse connectors. Some of the problems associated with transverse connectors include the need to pre-load connectors on a rod, high profiles, wide profiles, separate component fasteners, and proper tightening of threaded fasteners. Also, the ability of a transverse connector to connect rods that are skewed relative to each other may be problematic.

Some transverse connectors have engaging members that must be preloaded onto a rod prior to the rod being placed within a patient. The use of preloaded connectors may require significant pre-operative planning. The use of preloaded connectors may inhibit a surgical team's ability to make changes that are needed to meet conditions presented during insertion of the stabilization system in the patient. Other transverse connectors include rod openings that allow the transverse connector to be placed on rods after the rods have been attached by fixation elements to a patient.

Some transverse connectors may have a high profile and/or a wide profile. These profiles may cause surgical complications to tissue and bone adjacent to the connector. A rod fastening system that attaches the transverse connector to the adjacent rods may cause a high or wide profile. For example, a connector that snaps onto a spinal rod may be attached to a transverse connector by a nut that engages a threaded shaft of the connector. The nut and shaft may cause the assembled transverse connector to have a high profile and a wide profile. A high profile transverse connector may result in abrasion of tissue adjacent to the transverse connector. A wide profile transverse connector may require the removal of a portion of bone to allow the transverse connector to be attached to stabilization rods. A slim profile may require less or no bone removal when the transverse connector is attached to stabilization rods.

Some transverse connector rod fastening systems may require separate component fastening members to securely attach the transverse connector to stabilization rods. A separate component fastener, such as a nut, may be difficult to properly position and secure during an installation procedure.

A transverse connector must be securely tightened to a stabilization rod. Some rod fastening systems of transverse connectors use threaded fasteners to attach the transverse connector to adjacent rods. The threaded fastener typically is a setscrew or a nut. Not tightening a threaded fastener enough may allow movement of the transverse connector. Over tightening a threaded fastener may result in damage to the fastening system that could cause failure of the transverse connector. Applying a proper amount of torque to a threaded fastener may require the use of a torque wrench. Using a torque wrench may be burdensome to a surgical team that installs a stabilization system. Also, a torque wrench may require frequent calibration to ensure that an indicated amount of torque is applied when the torque wrench is used.

A threaded fastener such as a setscrew may need to be angled within the body so that a contact portion engages a rod sufficiently to secure the rod to the transverse connector. One type of transverse connector that utilizes a setscrew operates by contacting the setscrew against a lower portion of a rod to drive a top portion of the rod against a body of the transverse connector. The angle of the setscrew may be less than about 45° with respect to a longitudinal axis of the transverse connector. The angle of the setscrew may require an insertion tool with a flexible shaft to fix the rod to the transverse connector. Alternately, a large opening may be made in the patient so that an insertion tool without a flexible shaft may be used to fix the rod to the transverse connector. Another type of transverse connector that utilizes a setscrew operates by contacting the setscrew against an upper portion of a rod to drive a lower portion of the rod against a body of the transverse connector. Positioning a pair of rods within such a transverse connector may be difficult during installation of the transverse connector in a patient.

A transverse connector may include a body, a pair of rod openings in the body, and rod engagers. The body of the transverse connector may span a distance between a pair of rods. The body may have a fixed length, or the length of the body may be adjustable. Bending the body may adjust the length of the body and the orientation of the rod openings relative to the rods. Alternately, the length of the body may be adjustable by adjusting a position of a first section of the body relative to a second section of the body. After the positions of the first section and the second section are adjusted, the first section and the second section may be fixed using a fastener. The fastener may be, but is not limited to, a setscrew or a nut and bolt. The pair of rod openings may hold rods of a bone stabilization system. The rod engagers may be used to attach rods that are positioned in the rod openings to the body of the transverse connector.

A pair of rods of a stabilization system may be skewed relative to each other in both a vertical plane and a horizontal plane. Some transverse connectors cannot be adjusted to accommodate rods that are horizontally and/or vertically skewed. Other transverse connectors require a portion of the transverse connector to be bent to accommodate the skew of the rods.

A distance between a pair of rods of an orthopedic stabilization system may determine positions of rod fastening systems within a transverse connector. For transverse connectors that are attached to a pair of closely spaced rods, the rod fastening systems may be located on outer sides of the rod openings. For transverse connectors that are attached to a pair of rods that are spaced a farther distance apart, one rod fastening system may be located on an outer side of a rod opening and the other rod fastening system may be located between the two rod openings. Alternately, both rod fastening systems may be located between the rod openings. Also, for transverse connectors that are attached to a pair of rods that are spaced a large distance apart, an adjustable length transverse connector may be used.

SUMMARY OF THE INVENTION

Transverse connectors may be used to stabilize and inhibit movement of an orthopedic stabilization system. A transverse connector may be a fixed length transverse connector or an adjustable transverse connector. An embodiment of a fixed length transverse connector has a body configured to resist bending of the transverse connector. An alternate embodiment of a fixed length transverse connector is configured to allow the body to be bent to allow elongated member openings of the connector to be oriented relative to elongated members. Bending the fixed length transverse connector may also allow for some length adjustment of the transverse connector. A bendable fixed length transverse connector may include indentations that facilitate bending the transverse connector. An adjustable transverse connector may allow for adjustment of axial position, rotation, and/or angulation of a first elongated member opening relative to a second elongated member opening.

A transverse connector may include a pair of fastening systems configured to couple the transverse connector to elongated members. A fastening system may be a cam system. The cam system may include a contact surface that engages an elongated member or an elongated member engager when the cam system is activated to couple the transverse connector to the elongated member. Rotating the cam system may activate the cam system. A rotation activated cam system preferably does not include a threaded connection to the transverse connector so that rotating the cam system does not axially advance the cam system within the transverse connector.

Elongated members of an orthopedic stabilization system may be, but are not limited to, circular rods or rods having other cross sectional geometries. Elongated members may be two separate contoured members that are positioned on opposite sides of a bone or bones that are to be stabilized. In an alternate embodiment, the elongated members may be two ends of a single bent and contoured elongated member. The elongated members may be coupled to the bone or bones by fixation elements. The fixation elements may be, but are not limited to, bone screw connectors, hooks, or cable systems. An end portion of a transverse connector may be configured to attach to a fastening system of the fixation element that couples the fixation element to an elongated member. An opposite end portion of the transverse connector may include an elongated member opening adapted to couple the transverse connector to an elongated member. For example, a threaded shaft extending from a fixation element may extend through a slot or hole in an end portion of the transverse connector. A nut may be coupled and tightened to the shaft to secure the transverse connector to the fixation element. An opposite end portion of the transverse connector may include an elongated rod opening and a cam system that extends a rod engager against an elongated member positioned within the opening. Positioning an elongated member in the elongated member opening and activating the cam mechanism secures the transverse connector to the elongated member positioned within the elongated member opening.

A transverse connector may include a pair of elongated member openings. The elongated member openings may include open sections that allow the elongated member openings to be top loaded onto elongated members. The elongated members may be attached by fixation elements to a patient before the transverse connector is coupled to the elongated members. In an alternate embodiment, an elongated member opening may not include an open section that allows the elongated member opening to be top loaded onto an elongated member. To use a transverse connector that does not include an open section in an elongated member opening, the elongated member opening is placed over an end of the elongated member and maneuvered to a desired location before the elongated member is attached within the patient by fixation elements.

A fastening system of a transverse connector may be a cam system. The cam system may extend an engager into an elongated member opening of the transverse connector. The engager may secure the transverse connector to an elongated member positioned in the elongated member opening. An upper portion of the cam system may reside substantially within a body of the transverse connector to maintain a low profile of the transverse connector. A cam system may be unthreaded so that the cam system does not axially advance into or out of the transverse connector during use. In an embodiment, the cam system includes a cam that contacts the elongated member when the cam system is engaged. In alternate embodiments, a cam system may contact a separate component engager that extends into an elongated member opening to secure an elongated member to the transverse connector.

A cam system may be angled within a body of a transverse connector so that the transverse connector has a low profile. Placing the cam system at an angle within the body may allow for a strong connection between an elongated member and the transverse connector. The angle of the cam system within the body may allow for easy insertion of a drive tool within the cam system without the need to have a wide surgical opening in a patient. The cam system may be angled within the body at an angle in a range from about 45° to 90° with respect to a longitudinal axis of the transverse connector, and may preferably be angled about 70° with respect to the longitudinal axis of the transverse connector.

Portions of a cam system and portions of a body of a transverse connector may lock the cam system within the body to inhibit removal of the cam system from the body. Having the cam systems locked within the body makes the cam systems of the transverse connector unitary members of the transverse connector. The transverse connector may be provided to a surgeon as a single unit that includes no separate pieces that need to be attached to the transverse connector during installation of the transverse connector within a patient. Also, the transverse connector has no pieces that may fall out of the connector during an installation of the transverse connector within the patient.

A cam system may include a tool opening that is adapted to accept a driving tool. The driving tool may be, but is not limited to, a diamond drive, a hex wrench, a star drive, a screwdriver, or a socket wrench. The driving tool may allow the transverse connector to be top tightened. Rotating the driving tool, and thus the cam system, may move the cam system from an initial position to an engaged position. In the engaged position, the cam system will securely couple an elongated member positioned within an elongated member opening to the transverse connector. The cam system may engage the elongated member when the cam system is rotated a specific number of degrees. The number of degrees may be a value within the range from about 10° to about 360°. In an embodiment, rotating the driving tool approximately 170° couples the elongated member to the transverse connector. The cam system may include a stop that inhibits movement of the cam system beyond the engaged position.

A tool opening in a cam system may be keyed to accept a driving tool only in a specific orientation. The specific orientation may provide a user with a visual indication that the cam system is fully engaged when the drive tool is used to rotate the cam system. For example, the tool opening may be adapted to accept a diamond drive that can only be inserted into the tool opening in certain preferred orientations. When the diamond drive is inserted into the tool opening, a handle of the drive tool may be oriented at an angle relative to an elongated member positioned in an elongated member opening adjacent to the cam system. The drive tool may be rotated to rotate the cam system to an engaged position. The handle of the drive tool may be oriented substantially parallel to the elongated member when the cam system is in the engaged position. The orientation of the drive tool handle before and after rotation may be a visual indication to a user that the cam system has been activated to secure the elongated member to the transverse connector. A diamond drive may also provide a large contact area between a head of the drive tool and side walls of the tool opening. The large contact area may inhibit stripping or deformation of the tool opening during use. In alternate embodiments, the tool opening may be slotted, and the drive tool may include protrusions that fit within the slots only when a handle of the drive tool is in a specific orientation.

An engager of the cam system may be a cam that extends into an elongated member opening when the cam system is rotated. When the cam system is in an initial orientation, the engager may be positioned so that the engager does not extend into the elongated member opening of the transverse connector. In an alternate embodiment, a cam surface of the cam system may contact a separate component engager that extends into the elongated member opening when the cam system is engaged.

A surface of an elongated member opening, a contact surface of an engager, and/or an elongated member may be textured to inhibit movement of the transverse connector relative to the elongated member when a cam system couples the transverse connector to the elongated member. The engager may dimple the elongated member when the cam system is engaged to couple the elongated member to the transverse connector.

A fixed length transverse connector may include a body, a pair of elongated member openings and a pair of cam systems configured to couple elongated members to the transverse connector. The body of the transverse connector may include indentations that allow the transverse connector to be bent. Bending the transverse connector may allow for minor adjustment of a separation distance between elongated member openings of the transverse connector. Bending the transverse connector may also allow the elongated member openings to be properly oriented relative to elongated members of an orthopedic stabilization system so that there is a large contact area between an elongated member and an elongated member opening.

For fixed length transverse connectors that have small separation distances between the elongated member openings, one or both cam systems of the transverse connectors may be positioned so that the cam systems are not located between the elongated member openings. A cam system that is not located between the elongated member openings of a transverse connector is referred to as an outward positioned cam system. In embodiments, fixed length transverse connectors having separation distances between centers of the elongated member openings less than about 23 millimeters (mm) may have at least one outward positioned cam system.

For fixed length transverse connectors that have larger separation distances between the elongated member openings, the cam systems may be located between the elongated member openings of the transverse connector. In embodiments, fixed length transverse connectors having separation distances between centers of the elongated member openings greater than about 23 mm may have cam systems positioned between elongated member openings of the transverse connector. Transverse connectors may be provided in incremental lengths up to lengths between centers of elongated member openings of about 40 mm. Longer transverse connectors may also be formed.

An adjustable transverse connector may securely connect a pair of adjacent elongated member in a bone stabilization system. A pair of adjacent elongated member may be attached by fixation elements to a bone or bones within a patient. The elongated member may be skewed relative to each other. The transverse connector may be adjustable to accommodate variations in placement of adjacent elongated members. The transverse connector may be adjusted by adjusting a position of a first section of the transverse connector relative to a second section of the transverse connector. In an embodiment, the first section and the second section of an adjustable transverse connector may be adjusted relative to each other about at least two axes. In an alternate embodiment, the first section and the second section of an adjustable transverse connector may be adjusted relative to each other about at least three axes. After the positions of the first section and the second section are adjusted, a fastener may fix the position of the first section relative to the second section.

In an embodiment, an adjustable transverse connector may allow for adjustment of a distance between elongated member openings and for rotation of a first elongated member opening relative to a second elongated member opening. A first section of the transverse connector may include a shaft that telescopically fits within a hollow shaft of a second section of the transverse connector. Sliding the shaft of the first section within the hollow shaft of the second shaft allows for adjustment of the separation distance between elongated member openings of the transverse connector. An end of the first section shaft may be flared to inhibit removal of the shaft from the hollow section. The first shaft may be turned within the hollow shaft to allow the first elongated member to be rotated relative to the second elongated member. The hollow shaft may include a collet. A collar may be compression locked to the collet to inhibit movement of the first section relative to the second section. The collar may include a tab that fits within a slot of the collet. The tab and slot combination locates the collar relative to the collet so that a compression locking instrument may be easily positioned and used to lock the collar to the collet without undue manipulation of the collar.

An embodiment of a transverse connector may allow a length, a rotation angle, and an angulation angle between a first section of the transverse connector and a second section of the transverse connector to be adjusted. When the transverse connector is properly adjusted, tightening a fastener inhibits motion of the first section relative to the second section. The fastener of a transverse connector may be a component of a fastening system. The fastening system may include a lining. The lining may be, but is not limited to a bushing or a sleeve. The lining may be positioned within the second section of the transverse connector. The first section of the transverse connector may be positioned through the lining and the second section.

To adjust a length of a transverse connector, a distance between an elongated member opening in the first section and an elongated member opening in the second section may be adjusted by moving the elongated member opening of the first section towards or away from the elongated member opening of the second section. A transverse connector may allow adjustment of the length of the transverse connector within a limited range. For example, an embodiment of a transverse connector may have an adjustment range between centers of elongated member openings of from about 37 mm to 44 mm, another embodiment may have an adjustment range of from about 43 mm to 51 mm, another embodiment may have an adjustment range of from about 50 mm to 65 mm, and another embodiment may have an adjustment range of from about 61 to 80 mm. Other adjustment ranges may also be used.

An opening through the second section may be sized to allow the first section to be angled relative to the second section. A width of the opening may allow only a limited range of angulation between the first section and the second section. For example, the width of the opening may allow the angulation of the first section relative to the second section from about 0° to about 18°. An opening may be positioned through the second section so that smaller or larger angulation ranges are possible. For example, the width of the opening may allow the angulation of the first section relative to the second section in a range of from 0° to 10°, or in a range from 0° to 30°. The opening may be offset from a longitudinal axis of the second section so that the angulation of the first section relative to the second section does not have a lower limit of 0°. For example, the opening of the second section may allow an angulation range of from 10° to 35°. In other embodiments, different angulation ranges and limits for the angulation ranges are possible. If a transverse connector cannot be angulated in the direction of a desired orientation, a section that is placed over an elongated member may be removed from the elongated member and placed on the opposite elongated member to allow the transverse connector to be angulated in the desired direction.

An opening may also allow the first section to rotate relative to the second section. The first section may include a shaft that has a flat portion. A height of the opening in the second section may be sized so that an edge of the flat portion of the shaft engages the second section when a user attempts to rotate the first section beyond a limited rotation range. The engagement between the shaft and the second section may limit the range of rotational motion of the first section relative to the second section. In an embodiment, the first section is configured to rotate plus or minus 10° relative to the second section. In other embodiments, the rotational range of motion may be greater or less than plus or minus 10°. For example, the rotation of the first section relative to the second section may be limited to plus or minus 5°, or the rotation of the first section relative to the second section may be limited to plus or minus 20°. Other embodiments may have different rotational limits.

When the position of the first section relative to the second position is properly adjusted, the position may be set by tightening a fastener of the fastener system. In an embodiment, the fastener is a setscrew that pushes against a lining. Tightening the fastener creates shear forces between the setscrew, the lining, the first section, and the second section. The shear forces inhibit motion of the first section relative to the second section. The fastener may be another type of fastener, including, but not limited to, a nut or a cam member.

An adjustable transverse connector may include a fastening system that securely attaches the transverse connector to an elongated member of an orthopedic stabilization system. In an embodiment, the fastening system is a cam system. In alternate embodiments the fastening system may be, but is not limited to, a setscrew, a clamping system, or a nut and threaded fastener.

A first section and a second section of the transverse connector may be configured to be inseparable after assembly. A fastener used to fix the position of the first section of the body and the second section of the body may be threaded into the transverse connector. In an embodiment, the fastener may be inhibited from being removed from the transverse connector. The transverse connector may be supplied as an assembled unit to a surgeon who will install the transverse connector in a patient. Having fastening systems preinstalled in the transverse connector, the first section inseparable from the second section, and the fastener threaded on the transverse connector makes the transverse connector a unitary structure. The unitary structure transverse connector may be easy to install within a patient because the transverse connector includes no separate pieces that need to be attached during installation within a patient. Also, the unitary structure has no pieces that may fall out of the connector, be misplaced, be cross threaded, or be incorrectly positioned during an installation procedure within the patient.

A drive tool used to tighten a fastener that secures a first section of a transverse connector to a second section of the transverse connector may be the same instrument that is used to tighten fastening systems that couple elongated members to the transverse connectors. Using the same instrument to tighten the fastener and engage the cam system may minimize the instrument set needed to install a transverse connector within a patient. If the fastener that secures the first section of the transverse connector to the second section of the transverse connector is a threaded connector, a torque wrench may be attached to the drive tool so that a proper amount of torque may be applied to the fastener.

When a fastener that inhibits motion of a first section of a transverse connector relative to a second section of the transverse connector or a fastening system that couples an elongated member to the transverse connector is tightened, a counter-torque wrench may be coupled to the transverse connector. The counter-torque wrench allows the application of an offset torque to the transverse connector. The offset torque may prevent undesired movement of a stabilization system or patient when the fastener or a fastening system is rotated.

An advantage of a fixed length transverse connector is that the transverse connector may be a unitary structure that has no removable parts. The transverse connector may be top loaded onto elongated members. The absence of removable parts, such as setscrews or fasteners, may allow the transverse connector to be easily and quickly installed within a patient. The unitary structure also has no parts that can fall out of the transverse connector, be misplaced, be cross threaded, or be incorrectly positioned during installation.

An advantage of an adjustable transverse connector is that the transverse connector may be supplied to a surgeon as a single unit. The transverse connector may be top loaded onto elongated members. The unit has no separable parts, and if the unit includes threaded members, the threaded members may be pre-attached to the unit. Pre-attaching threaded members to the unit avoids the need to thread the parts into the unit during installation within the patient.

An advantage of a transverse connector that uses cam systems to couple the transverse connector to elongated members is that the transverse connector may be attached to the elongated members without the use of threaded fasteners. The absence of threaded fasteners allows the connector to be attached to an elongated member without the transverse connector being under-tightened or over-tightened. The cam system may include an indicator that informs the user when the transverse connector is properly fastened to an elongated member. The indicator may be a visual indication, such as a position of a driving tool, and/or the indicator may be a vibrational signal transmitted to the user when the cam system is activated.

An advantage of transverse connectors is that several sizes of fixed length connectors and several adjustable transverse connectors may be provided to a surgeon who will install a stabilization system within a patient. The different types and sizes of transverse connectors may allow a surgeon to install a stabilization system that best fits a patient.

An advantage of an adjustable transverse connector is that the connector may be used to connect orthopedic rods that are not oriented parallel to each other. The transverse rod may be used to connect rods that are not horizontally parallel and/or vertically parallel. The transverse connector may also be used to connect rods that are oriented parallel to each other.

Another advantage of a transverse connector is that the transverse connector may have a thin and low profile. The low profile of the transverse connector may allow the transverse connector to have a minimal effect on adjacent tissue when the transverse connector is installed within a patient. The thin profile may allow the transverse connector to be easily positioned at desired locations on a stabilization system. Further advantages of transverse connectors may include that the transverse connectors are sturdy, durable, light weight, simple, efficient, reliable and inexpensive; yet the transverse connectors may also be easy to manufacture, install, and use.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
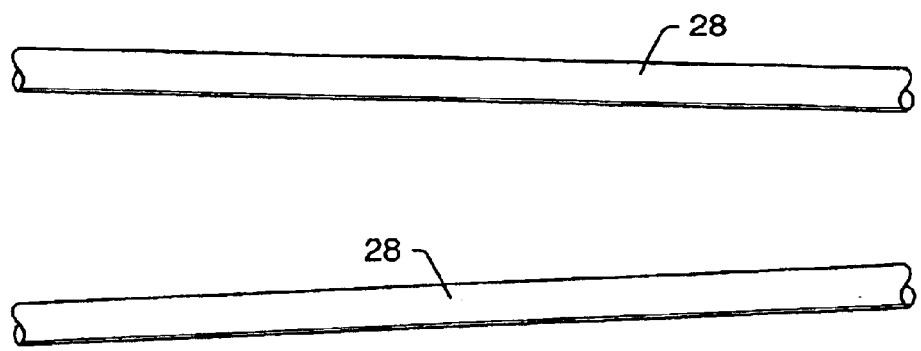
FIG. 1 is a top elevational view of a pair of horizontally skewed rods.
Figure 2:
FIG. 2 is a front elevational view of a pair of vertically skewed rods.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 3:
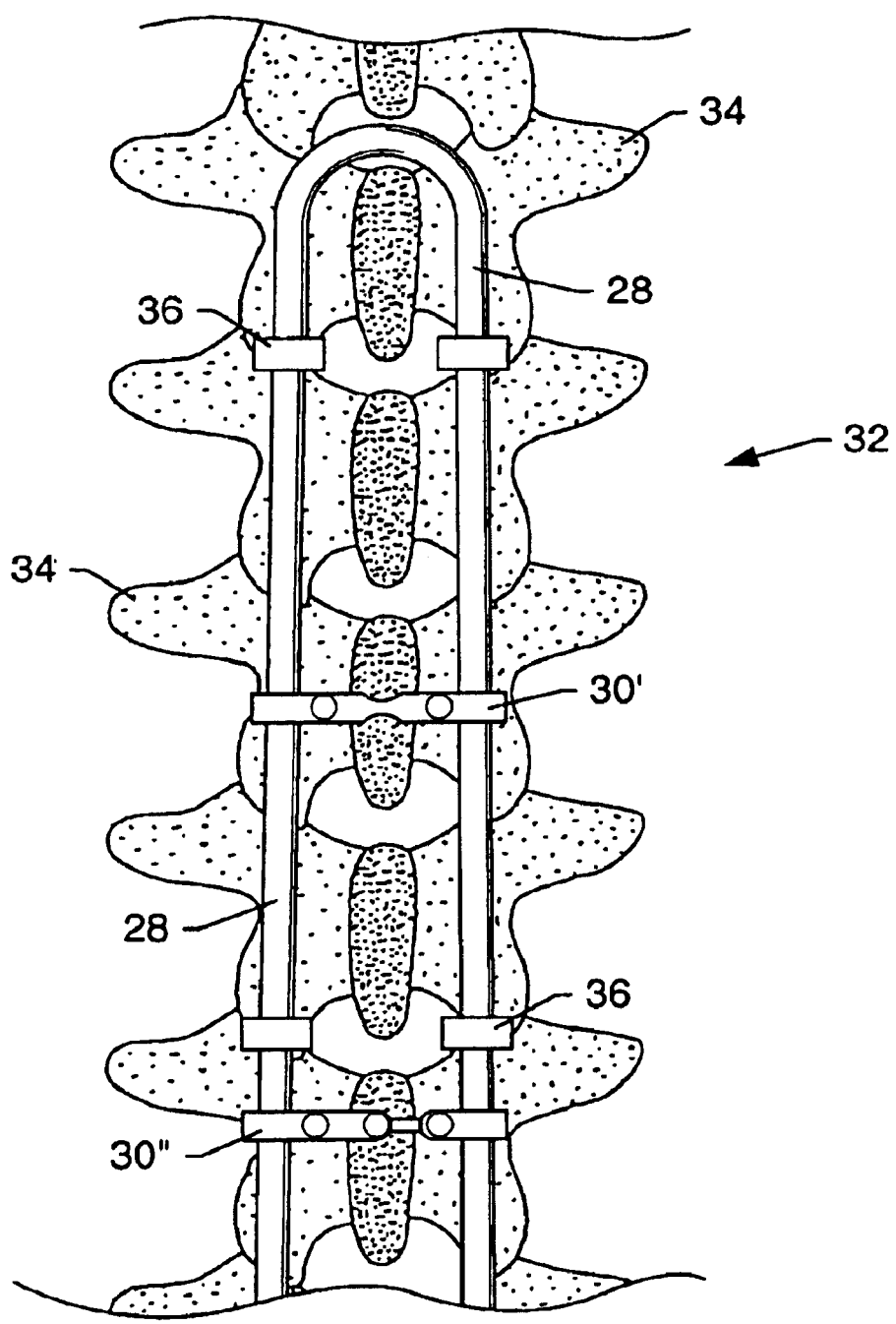
FIG. 3 is a top elevational view of a portion of a spinal stabilization system.

With reference to the drawings, transverse connectors are denoted generally as 30. Transverse connectors 30 may be used to connect elongated members 28 of an orthopedic stabilization system 32 together. Transverse connectors 30 may provide rigidity to the orthopedic stabilization system 32. Transverse connectors 30 may also inhibit undesired motion of the orthopedic stabilization system 32. Transverse connectors 30 may be fixed length transverse connectors or adjustable length transverse connectors. The elongated members 28 of an orthopedic stabilization system 32 may be coupled to bones 34 by fixation elements 36. The fixation elements 36 may be, but are not limited to, hooks and bone screw connectors. In an embodiment, the elongated members 28 are spinal rods that are coupled to vertebral bodies 34 by fixation elements 36. The spinal rods 28, fixation elements 36, and transverse connectors 30 form part of a spinal stabilization system 32. FIG. 3 shows a portion of an embodiment of a spinal stabilization system 32.

Elongated members 28 of an orthopedic stabilization system 32 may be, but are not limited to, circular rods or rods having other cross sectional geometries. Other types of cross sectional geometries for elongated members 28 may include, but are not limited to, oval, rectangular, or polygonal shaped cross sectional areas. Elongated members 28 may be two separate contoured members that are positioned on opposite sides of a bone or bones 34 that are to be stabilized. In an alternate embodiment, the elongated members 28 may be two ends of a single bent and contoured elongated member. The elongated members 28 shown in FIG. 3 are two ends of a single bent and contoured elongated member.

Figure 4:
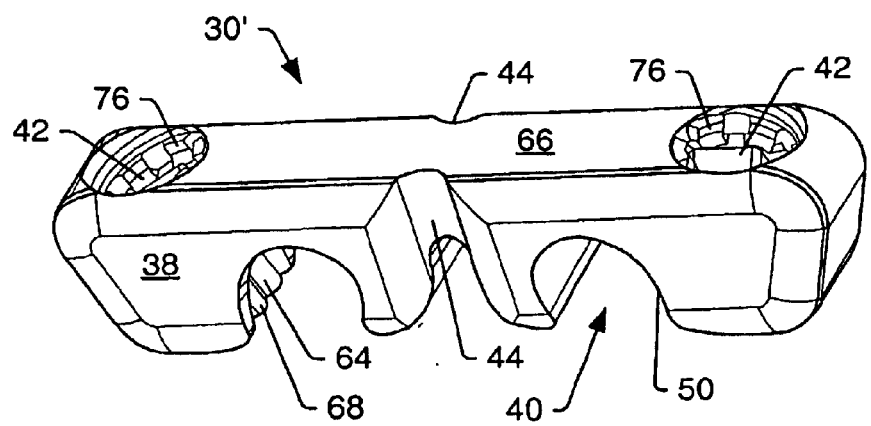
FIG. 4 is a perspective view of a transverse connector with cam systems that are not positioned between elongated member openings in the transverse connector.
Figure 5:
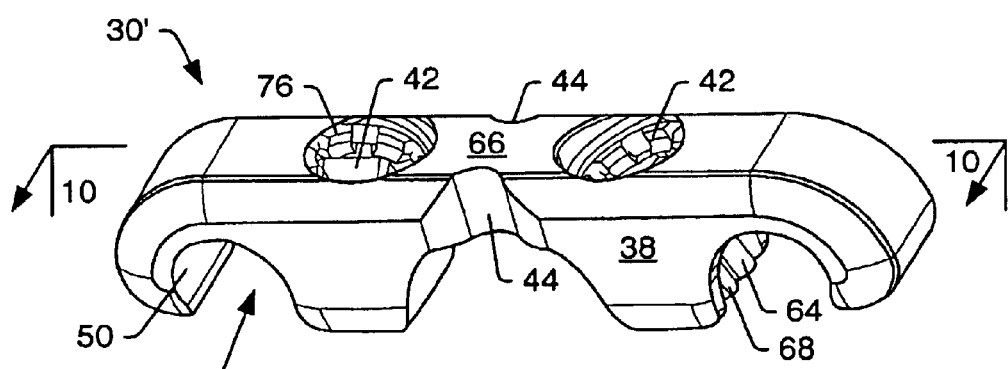
FIG. 5 is a perspective view of a transverse connector with cam systems that are positioned between elongated member openings in the transverse connector.
Figure 6:
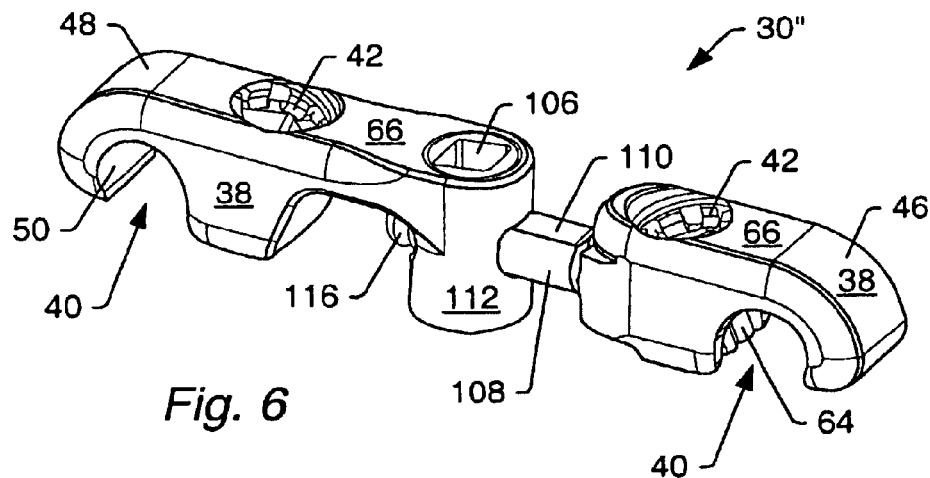
FIG. 6 is a perspective view of an adjustable transverse connector that may be adjusted about three degrees of freedom.
Figure 7:
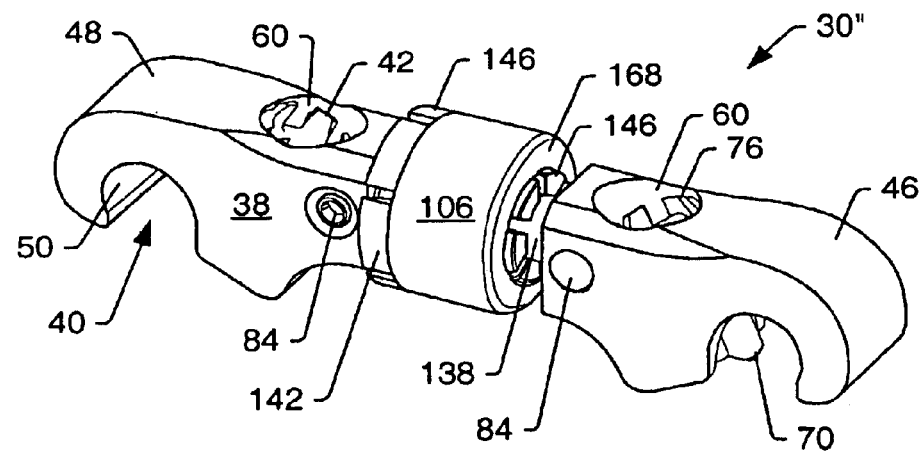
FIG. 7 is a perspective view of an adjustable transverse connector that may be adjusted about two degrees of freedom.

A transverse connector 30 may include body 38, a pair of elongated member openings 40, and fastening systems 42 that couple the transverse connector to elongated members 28. The fastening systems 42 may be cam systems. The body 38 of the transverse connector 30 spans a distance between a pair of elongated members 28 of an orthopedic stabilization system 32 during use. A body 38 of a fixed length transverse connector 30' may be a single member that optionally includes at least one indented surface 44. FIGS. 4 and 5 show embodiments of fixed length transverse connectors 30'. A body 38 of an adjustable transverse connector 30" may include first section 46 and second section 48. The position of the first section 46 may be adjustable relative to the position of the second section 48. FIGS. 6 and 7 show embodiments of adjustable length transverse connectors 30". The components of a transverse connector 30 may be made of biocompatible material including, but not limited to titanium, titanium alloys, stainless steel and ceramics.

A transverse connector 30 may include a pair of elongated member openings 40. Surfaces 50 of the elongated member openings 40 may closely conform to a shape of an exterior surface of an elongated member 28 so that a tight fit is formed between the surface and the elongated member when the transverse connector 30 is coupled to the elongated member. The elongated member openings 40 may include open sections that allow the elongated member openings to be top loaded onto elongated members 28. The elongated members 28 may be attached by fixation elements 36 to a patient before the transverse connector 30 is coupled to the elongated members. In an alternate embodiment, an elongated member opening 40 may not include an open section that allows the elongated member opening to be top loaded onto an elongated member 28. To use a transverse connector 30 that does not include an open section in an elongated member opening 40, the elongated member opening is placed over an end of the elongated member 28 and maneuvered to a desired location before the elongated member is attached within the patient by fixation elements 36.

Figure 8:
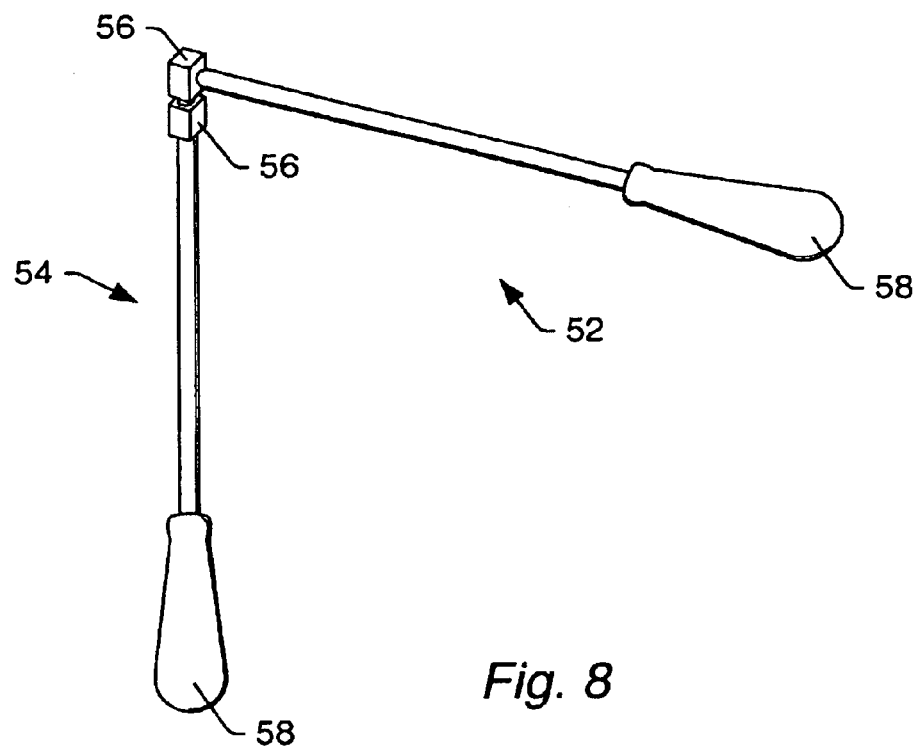
FIG. 8 shows a perspective view of a pair of transverse connector benders.
Figure 9:
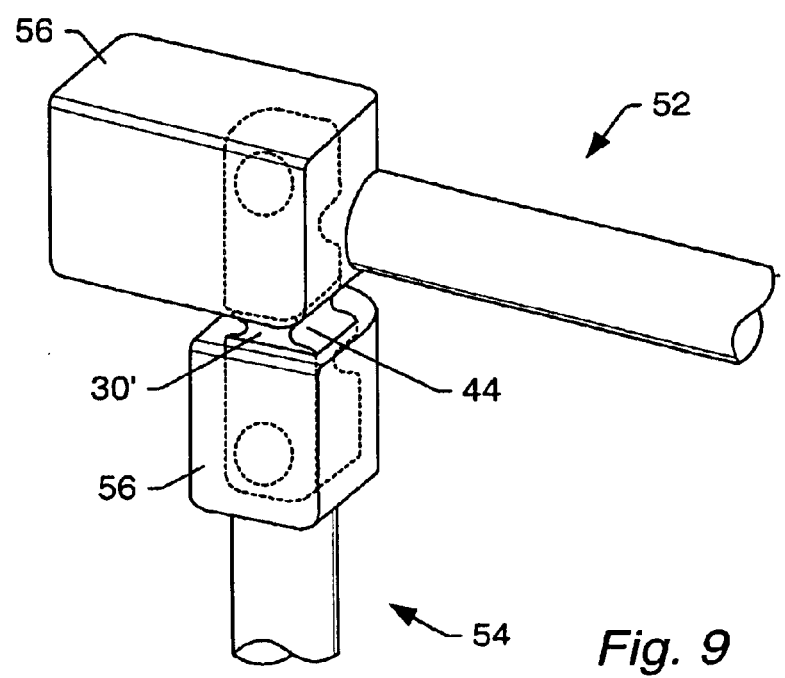
FIG. 9 shows a detailed view of the heads of a pair of benders with a transverse connector positioned within the benders.

A fixed length transverse connector 30' may include a body 38, a pair of elongated member openings 40, and a pair of cam systems 42 configured to couple the transverse connector to elongated members 28. The body 38 of the transverse connector 30' may include indentations 44 that allow the transverse connector to be bent. Bending the transverse connector 30' may allow for minor adjustment of a separation distance between elongated member openings 40 of the transverse connector. Bending the transverse connector 30' may also allow the elongated member openings 40 to be properly oriented relative to elongated members 28 of an orthopedic stabilization system 32 so that there is a large contact area between an elongated member and an elongated member opening. FIG. 8 shows an embodiment of a pair of benders 52, 54 that may be used to adjust a transverse connector 30'. FIG. 9 shows a detail view of a transverse connector 30' positioned within heads 56 of the benders 52, 54. When a transverse connector 30' is placed within heads 56 of the benders 52, 54, handles 58 of the benders may be grasped and forced towards each other to bend the transverse connector.

For fixed length transverse connectors 30' that have small separation distances between the elongated member openings 40, one or both cam systems 42 of the transverse connectors may be positioned so that the cam systems are not located between the elongated member openings. A cam system 42 that is not located between the elongated member openings 40 of a transverse connector 30' is referred to as an outward positioned cam system. In embodiments, fixed length transverse connectors 30' having separation distances between centers of the elongated member openings 40 less than about 80 mm may have at least one outward positioned cam system. Embodiments of transverse connectors 30' with outward positioned cam systems 42 may be produced in incrementally increasing sizes. For example, three sizes of transverse connectors 30' with outward positioned cam systems 42 may be produced in 5 mm increments with the smallest transverse connector having a separation distance between centers of elongated member openings 40 of about 10 mm. FIG. 4 shows an embodiment of a transverse connector 30' having outward positioned cam systems 42. Transverse connectors 30' having outward positioned cam systems 42 may also be produced in other size ranges and in different incremental lengths.

For fixed length transverse connectors 30' that have larger separation distances between the elongated member openings 40, the cam systems 42 may be located between the elongated member openings of the transverse connector. Fixed length transverse connectors 30' having separation distances between centers of the elongated member openings 40 greater than about 15 mm may have cam systems 42 positioned between elongated member openings of the transverse connector. Embodiments of transverse connectors 30' with cam systems 42 positioned between elongated member openings 40 may be produced in incrementally increasing sizes. For example, four sizes of transverse connectors 30' with cam systems 42 positioned between elongated member openings 40 may be produced in 5 mm increments with the smallest transverse connector having a separation distance between centers of elongated member openings of about 25 mm. FIG. 5 shows an embodiment of a transverse connector 30' having cam systems 42 positioned between elongated member openings 40. Transverse connectors 30 having cam systems 42 positioned between elongated member openings 40 may also be produced in other size ranges and in different incremental lengths.

Figure 10:
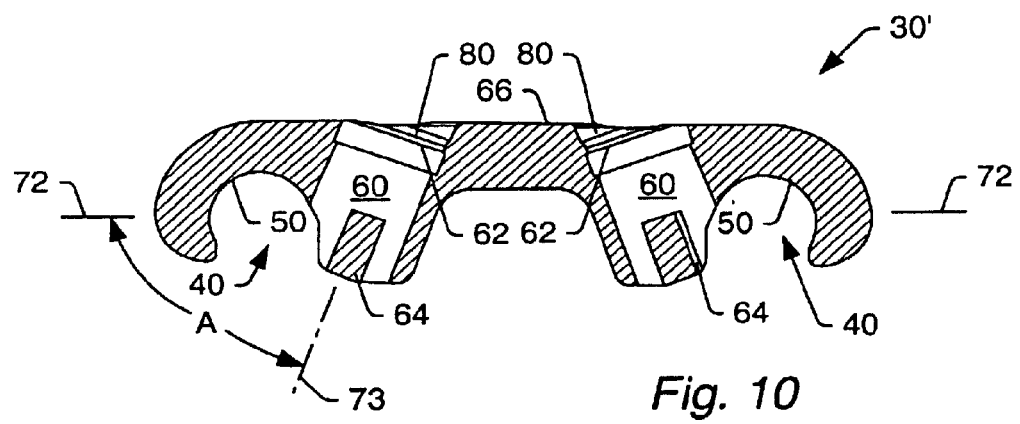
FIG. 10 is a cross sectional view of a transverse connector taken substantially along plane 10—10 of FIG. 5, without cam systems within the transverse connector.

FIG. 10 shows a cross sectional view of a fixed length transverse connector 30' without cam systems 42 positioned within cam system openings 60. Cam system openings 60 of a transverse connector 30 may include shoulders 62 and cam guides 64. The shoulders 62 provide surfaces that may inhibit removal of cam systems 42 that are positioned within the cam system openings 60. When a cam system 42 is inserted into a cam system opening 60, the cam system may be substantially contained within the body 38 so that the cam system does not extend a substantial distance above upper surface 66 of the body.

Figure 11:
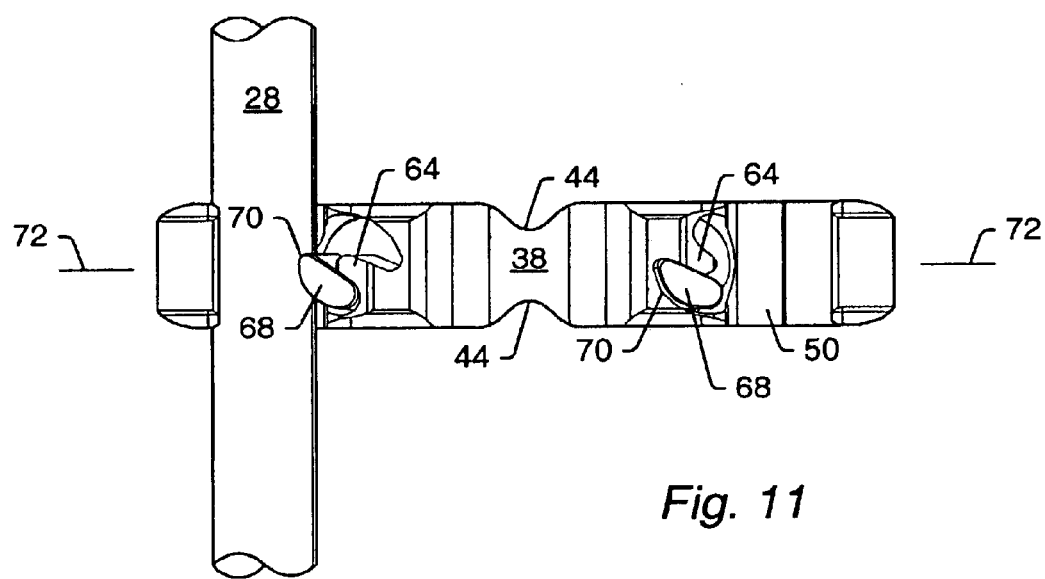
FIG. 11 is a bottom elevational view of a fixed length transverse connector.

Cam guides 64 may provide limits for rotational motion of cam systems 42 within cam system openings 60 of a transverse connector body 38. The cam guides 64 may also limit an insertion depth of the cam system 42 into the body 38. FIG. 11 shows a bottom view of an embodiment of a transverse connector 30' with cam guides 64.

A portion of a cam system opening 60 may be formed in an inner surface 50 that defines an elongated member opening 40 of the transverse connector 30. The portion of the cam system opening 60 formed in the inner surface 50 of the elongated member opening 40 allows engager 68 to extend into the elongated member opening 40 and contact an elongated member 28 positioned within the elongated member opening during use. In an embodiment, the engager 68 is cam surface 70 of the cam system 42.

Cam system openings 60 may be angled within the body 38 relative to a longitudinal axis 72 of the transverse connector 30. Alternately, the cam system openings 60 may be formed perpendicular to the longitudinal axis 72 of the transverse connector 30. An angled cam system opening 60 allows an engager 68 to contact an elongated member 28 below the mid point of the elongated member so that the engager may press an upper portion of the elongated member against surface 50 of the elongated member opening 40. A longitudinal axis 73 of a cam system opening 60 (and a longitudinal axis of a cam system 42 positioned within the opening) may be angled at an angle A with respect to the longitudinal axis 72 of the transverse connector 30, as shown in FIG. 10. A cam system opening 60, and a cam system 42 positioned within the opening, may be angled from about 45° to 90° relative to the longitudinal axis 72 of the transverse connector 30. Preferably, the cam system openings 60 are angled greater than 60° relative to the longitudinal axis 72 of the transverse connector 30. For example, in an embodiment, the cam system openings 60 are angled at 70° relative to the longitudinal axis 72 of the transverse connector 30. The large angle of the cam system opening 60 may allow for easy access to tool opening 74 of a cam system 42 positioned within the cam system opening. An opening in a body of other transverse connectors, such as a transverse connector shown in U.S. Pat. No. 5,947,966, may be formed at a significantly smaller angle relative to the longitudinal axis of the transverse connector, such as about 45°. The smaller angle of an opening in other transverse connectors may make accessing a tool opening more difficult and/or inconvenient during an installation procedure.

Figure 12:
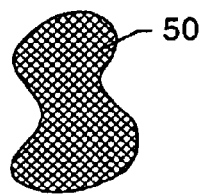
FIG. 12 is an elevational view of a textured surface portion of an elongated member opening surface of a transverse connector.

An initial manufacturing process that forms an elongated member 28 may form an outer surface of the elongated member as a smooth surface. A subsequent process may texture the outer surface of the elongated member 28. Similarly, an initial manufacturing process that forms a transverse connector 30 may form elongated member opening surfaces 50 as smooth surfaces. A subsequent process may texture the elongated member opening surfaces 50. Also, elongated member contact surfaces of engagers 68 may be textured. Texturing an outer surface of an elongated member 28, elongated member opening surfaces 50, and/or contact surfaces of engagers 68 may provide large coefficients of friction between the elongated member and the transverse connector 30 as compared to similar smooth surfaces so that motion of the elongated member is inhibited when the transverse connector is coupled to the elongated member. The outer surface of an elongated member 28, elongated member opening surfaces 50, or contact surfaces of engagers 68 may be textured by any texturing process, including but not limited to, scoring the surface, a ball peening process, an electric discharge process, or embedding hard particles within the surface. FIG. 12 shows an embodiment of a portion of a textured elongated member opening surface 50 of an elongated member opening that has a scored surface.

Figure 13:
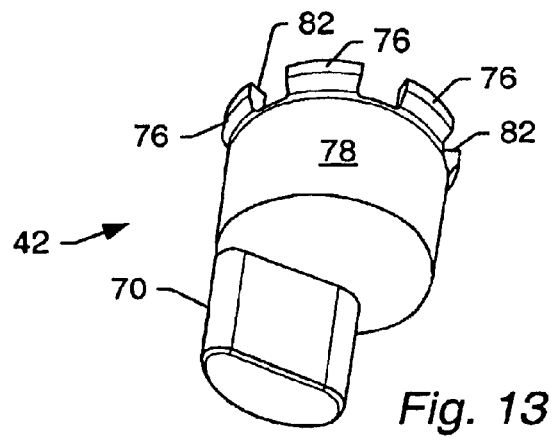
FIG. 13 is a perspective view of a cam system.

FIG. 13 shows an embodiment of a cam system 42 that is positionable within a cam system opening 60 of a transverse connector 30. The cam system 42 may include protrusions 76, main body 78, and cam surface 70. When a cam system 42 is inserted into a cam system opening 60, wall 80 of the cam system opening (shown in FIG. 10) may compress all of the protrusions 76 inwards. The protrusions 76 may snap back to their original configuration when upper surfaces 82 of the protrusions 76 pass the shoulder 62 of the cam system opening 60. If a force is applied to the cam system 42 that tends to force the cam system out of the cam system opening 60, the upper surfaces 82 may engage the shoulder 62 to inhibit removal of the cam system from the cam system opening.

FIG. 7 shows an embodiment of a transverse connector 30 that includes a vibrational indicator that informs a user that a cam system 42 has been engaged. The transverse connector 30 includes pin 84 positioned through the transverse connector body 38 so that a portion of the pin extends into a cam system opening 60 adjacent to protrusions 76 of the cam system 42. If the cam system 42 is rotated, a protrusion 76 will contact the pin 84 so that the protrusion is deflected inwards. When the edge of the deflected protrusion 76 passes the pin 84, the protrusion snaps back outwards and transmits a vibration through the transverse connector body 38. The vibration may be heard and/or felt by a user. The vibration may inform a user that the cam system 42 is being engaged. A certain number of vibrations may indicate to a user that the cam system 42 is fully engaged. For example, if there are six protrusions 76, and if the cam system 42 is fully engaged when the cam system is rotated 180°, three separate vibrations during rotation of the cam system would indicate that the cam system is fully engaged.

A main body 78 of a cam system 42 may fit within a cylindrical portion of a cam system opening 60. An insertion depth of the cam system 42 into a transverse connector body 38 may be limited when the main body 78 contacts a cam guide 64 of the transverse connector body. When a cam system 42 is placed within a cam system opening 60 so that the main body 78 contacts a cam guide 64, the upper surfaces 82 of the protrusions 76 may pass past the shoulder 62 of the cam system opening so that removal of the cam system from the cam system opening is inhibited.

Figure 14:
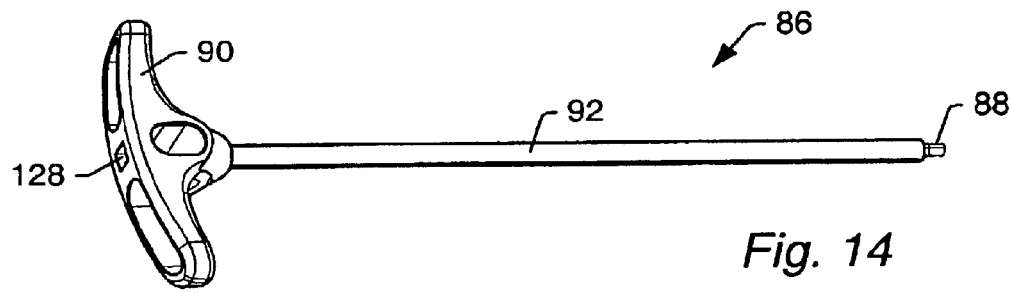
FIG. 14 is a perspective view of a drive tool that may be used to rotate a fastener and/or cam system of a transverse connector.
Figure 15:
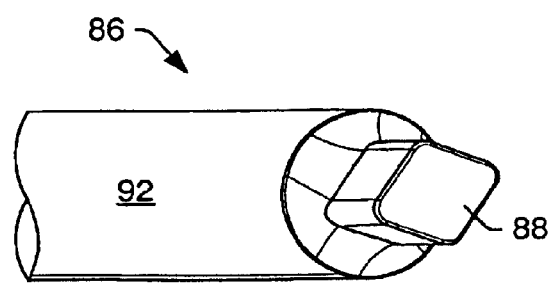
FIG. 15 is a perspective detail of drive head of the drive tool of FIG. 14.

Tool opening 74 may be formed in the main body 78. The tool opening 74 may allow insertion of drive tool 86 in the main body 78 so that the cam system 42 may be rotated. The tool opening 74 may be configured to accept drive head 88 of the drive tool 86. The drive tool 86 may be, but is not limited to, a diamond drive, a hex wrench, a star drive, a screwdriver, or a socket wrench. FIG. 14 shows an embodiment of a drive tool 86 that may be used to tighten a cam system 42 of a transverse connector 30. The drive tool 86 may include handle 90, shaft 92, and drive head 88. The handle 90 may be shaped so that a user may comfortably and securely grasp and use the drive tool 86. The handle 90 may have an elongated shape that can be aligned relative to the transverse connector 30 or an elongated member 28 to provide an indication during use that the transverse connector has been coupled to the elongated member. In an embodiment of a drive tool 86, the drive tool has a "T"-shaped handle 90, as shown in FIG. 14. The shaft 92 of the drive tool 86 may mechanically attach the handle 90 to the drive head 88. FIG. 15 shows a detail view of an embodiment of the drive head 88 of a diamond drive tool 86.

Figure 16:
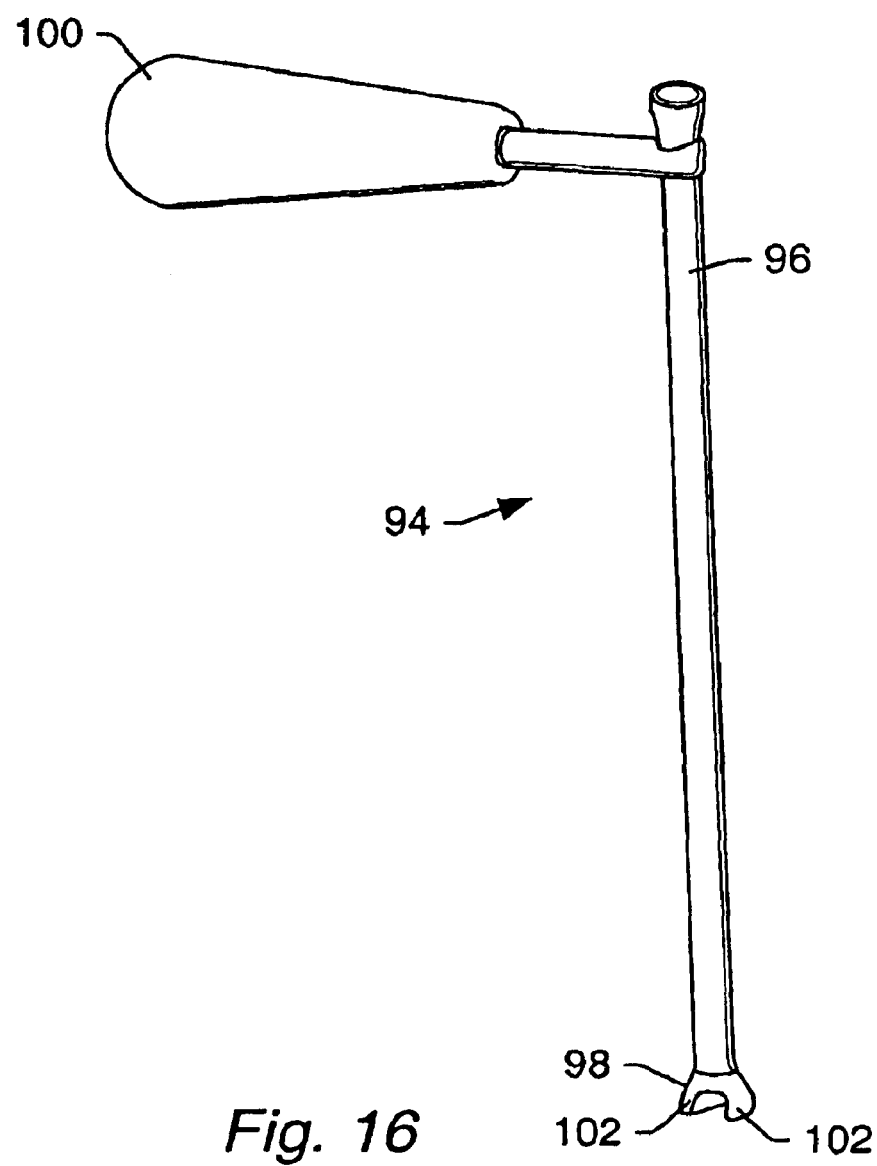
FIG. 16 is a perspective view of a torque limiting wrench.

FIG. 16 shows an embodiment of torque limiting wrench 94 that may be used when a cam system 42 of a transverse connector 30 is tightened. The torque limiting wrench 94 may inhibit undesired motion of a patient or parts of a stabilization system 32 when a cam system 42 is rotated. The torque limiting wrench 94 may include hollow shaft 96, head 98, and handle 100. A drive tool shaft 92 may be placed through the hollow shaft 96 and into a tool opening 74. The head 98 may be placed on the transverse connector 30 so that inner surfaces of the lips 102 of the head contact sides of the transverse connector. The drive tool 86 may be rotated one direction to apply a torque to a cam system 42. Force may be applied to the handle 100 in the opposite direction to counter the torque applied to the cam system 42.

A tool opening 74 of a cam system 42 may be configured to accept a drive tool 86 in an initial desired orientation. The diamond drive tool head 88 shown in FIG. 15 may be inserted into a tool opening 74 of a cam system 42 in only two orientations. In either orientation, handle 90 may be offset at an angle from an elongated member 28 positioned within an elongated member opening 40 of the transverse connector 30. Rotating the drive tool 86 rotates the cam system 42 so that an elongated member 28 positioned within an elongated member opening 40 adjacent to the cam system is secured to the transverse connector 30. A user may be able to feel resistance to turning that indicates that the transverse connector 30 is being securely coupled to the elongated member 28. A cam guide 64 of the transverse connector 30 may limit the rotation range of the cam system 42. The position of the handle 90 after rotation may provide a visual indication to a user that the transverse connector 30 has been securely coupled to the elongated member 28. In an embodiment, the handle 90 of the drive tool 86 is oriented substantially parallel to the elongated member 28 after the drive tool has been rotated to fully engage the transverse connector 30 to the elongated member. In other embodiments, the handle 90 may be substantially perpendicular to the elongated member 28 when the transverse connector 30 is fully engaged to the elongated member. Other types of visual indication systems may be used to determine when an elongated member 28 is secured to a transverse connector 30. For example, markings on the shaft 92 may align with markings on the transverse connector 30 to indicate that an elongated member 28 has been coupled to the transverse connector.

In an embodiment, a cam system 42 may fully engage a transverse connector 30 to an elongated member 28 when the cam system is rotated 170°. A handle 90 of a drive tool 86 may be initially offset from the elongated member 28 by about 10° when the drive tool head 88 is positioned in a tool opening 74 of the cam system 42. When the drive tool 86 is rotated 170° to secure the elongated member 28 to the transverse connector 30, the handle 90 may become substantially parallel to the elongated member. Embodiments of cam systems 42 may fully engage transverse connectors 30 to elongated member 28 when the cam systems are rotated less or greater than 170°. For example, in an embodiment, a cam system 42 is configured to fully engage a transverse connector 30 to an elongated member 28 when the cam system is rotated about 10°. In another embodiment, a cam system lock 42 is configured to fully engage a transverse connector 30 to an elongated member 28 when the cam system is rotated about 360°. Other embodiments of cam systems 42 may be configured to fully engage a transverse connector 30 to an elongated member 28 when the cam system is rotated to some desired value between 10° and 360°.

FIG. 11 shows a bottom view of an embodiment of a transverse connector 30. One engager 68 is shown fully engaged against an elongated member 28. Another engager 68 is shown in an initial or unengaged position. The cams 68 of the transverse connector 30 shown in the embodiment of FIG. 11 become fully engaged against an elongated member 28 when the cams systems 42 are rotated 170°.

To form a fixed length transverse connector 30', the body 38 of the transverse connector is machined to form elongated member openings 40, cam system openings 60 for cam systems 42, and cam guides 64. Indentions 44 may be formed in the body 38 to allow the transverse connector 30' to be bent. Cam systems 42 are also machined. The elongated member opening surfaces 50 and/or the contact surfaces of the engagers 68 may be textured so that the coefficient of friction between the surfaces and elongated members 28 placed against the surfaces will be high. The cam systems 42 may be inserted into the cam system openings 60 until the upper surfaces of the protrusions 76 pass the shoulders 62 of the cam system openings. When the cam systems 42 are inserted into the cam system openings 60, the transverse connector 30' is formed.

To establish a bone stabilization system 32, a pair of elongated members 28 may be coupled to the bone or bones 34 being stabilized. The elongated members 28 may be coupled to the bone or bones 34 by fixation elements 36 (shown in FIG. 3). A transverse connector 30' may be placed over the elongated members 28 so that the elongated members are positioned within elongated member openings 40 of the transverse connector 30 at a desired location. If necessary or desired, the transverse connector 30' may be bent with benders 52, 54 so that surfaces 50 of the elongated member openings 40 contact large areas of the elongated members 28. A torque limiting wrench 94 may be placed on the transverse connector 30, and a shaft 92 of a drive tool 86 may be inserted through the hollow shaft 96 of the torque limiting wrench. A head 88 of a drive tool 86 may be inserted into a tool opening 74 of a first cam system 42 of the transverse connector 30'. The drive tool 86 may be rotated to rotate the cam system 42. Rotating the cam system 42 may force an engager 68 into an elongated member opening 40 so that the engager presses an elongated member 28 against the surface 50 of the elongated member opening. The engager 68 may be a cam surface 70 of the cam system 42. The drive tool 86 may be removed from the tool opening 74 of the first cam system 42. The drive tool 86 and the torque limiting wrench 94 may be repositioned so that the drive tool head 88 is inserted into the tool opening 74 of the second cam system 42. The drive tool 86 may be rotated to force an engager 68 against the second elongated member 28 so that the engager presses the second elongated member against the second elongated member opening surface 50. Other transverse connectors 30 may be attached to the elongated members 28 at other locations along the lengths of the elongated members.

Figure 17:
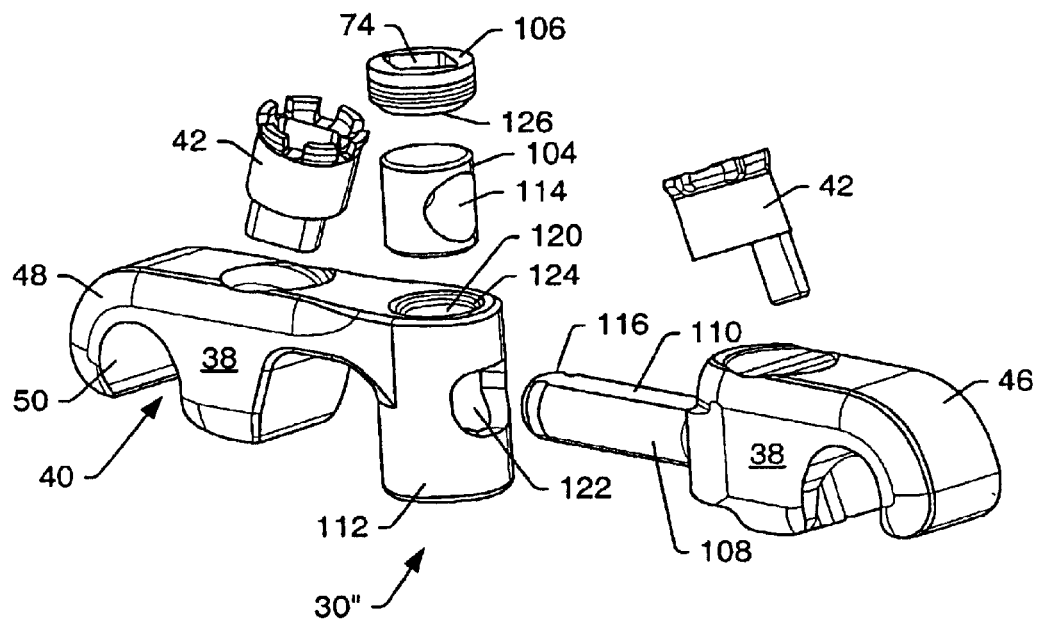
FIG. 17 is an exploded view of an adjustable transverse connector.

FIG. 17 shows an exploded view of an embodiment of an adjustable transverse connector 30". The adjustable transverse connector 30" may include first section 46, second section 48, optional lining 104, fastener 106, elongated member openings 40 and cam systems 42. The optional lining 104 may be, but is not limited to, a bushing or a sleeve. The fastener 106 may fix the position of the first section 46 relative to the second section 48. The cam systems 42 may securely fasten an elongated member 28 to a section 46 or 48 of the transverse connector 30". In alternate embodiments, an elongated member 28 may be fastened to a transverse connector 30" by connecting mechanisms other than cam systems 42. The other types of connecting mechanisms may include, but are not limited to, setscrews, and connector and nut arrangements. Combinations of different types of connecting mechanisms may also be used to couple a transverse connector 30" to an elongated member 28.

Figure 20:
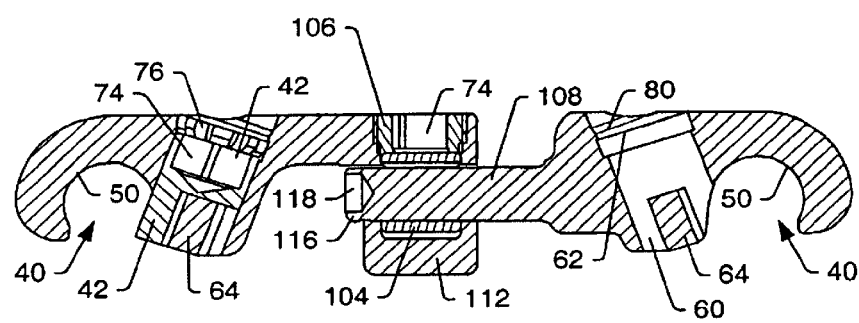
FIG. 20 is a cross sectional view of a transverse connector taken substantially along plane 20—20 of FIG. 19, with only one cam system within the transverse connector.

A first section 46 of an adjustable transverse connector 30" may include shaft 108. The shaft 108 may include flat surface 110. The shaft 108 may be inserted through a lining 104 positioned within holder 112 of a second section 48. The lining 104 may include circular bore 114. The bore 114 may have a diameter that is slightly larger than diameter D (shown in FIG. 22) of the shaft 108. End 116 of the shaft 108 may include countersunk opening 118 (as shown in FIG. 20) that allows the end to be peened after insertion through the holder 112 and lining 104. Peening the end 116 may inhibit removal of the lining 104 from the holder 112, and the first section 46 from the second section 48. A separation distance between centers of elongated member openings 40 of the transverse connector 30" may be adjusted by moving elongated member opening of the first section 46 towards or away from an elongated member opening of the second section 48.

Several different transverse connectors 30" may be formed with varying adjustment ranges. An adjustment range of a transverse connector 30" is the range through which a separation distance between centers of elongated member openings 40 may be adjusted. For example embodiments of transverse connectors 30" may be formed that have the following overlapping adjustment ranges.

| Transverse connector size | Adjustment range (mm) |
| --- | --- |
| 1 | 37–44 |
| 2 | 43–51 |
| 3 | 50–65 |
| 4 | 61–80 |

Other transverse cony be made that have different adjustment ranges.

A holder 112 of a second section 48 of an adjustable transverse connector 30" may include first opening 120 and second opening 122. The first opening 120 allows a lining 104 to be inserted into the holder 112 so that a bore 114 of the lining aligns with the second opening 122. In an embodiment, the first opening 120 may be a blind hole that does not extend completely through the holder 112. The second opening 122 allows a first section shaft 108 to be placed through the holder 112 and the lining 104. Placing a shaft 108 of the first section 46 through the holder 112 and the lining 104 inhibits removal of the lining from the holder.

A fastener 106 may be used to apply force to a lining 104 to inhibit movement of a first section 46 of an adjustable transverse connector 30" relative to a second section 48 of the transverse connector. In an embodiment, the fastener 106 is a setscrew that mates to threading 124 in an upper section of the holder 112. Tightening the setscrew 106 forces an end of the setscrew against a lining 104 to force a first section shaft 108 against the holder 112. The resulting forces between the setscrew 106, the lining 104, the shaft 108 and the holder 112 inhibit motion of the first section 46 relative to the second section 48. Other types of fasteners 106 may be used. For example, in an embodiment the fastener 106 may be a cam mechanisms that forces the lining 104 against the shaft 108 when the cam is engaged. In an alternate embodiment, the fastener 106 may be a nut that threads to a shaft extending from the lining 104. A counter torque may be applied to the transverse connector 30" by a torque limiting wrench 94 to inhibit movement of the transverse connector, stabilization system 32, or patient when the fastener 106 is tightened.

The fastener 106 may include tool opening 74. Drive head 88 of drive tool 86 may be inserted into the tool opening 74. The drive tool 86 may be rotated to rotate the fastener 106.

Rotating the fastener 106 in a clockwise direction may press end 126 of the fastener against a top of the lining 104. The end 126 of the fastener 106 may have a large surface area to provide a large contact area with the lining 104. The contact of the fastener 106 against the lining 104 may press a shaft 108 against a holder 112 so that the axial, angular, and rotational motion of a first section 46 of a transverse connector 30" relative to a second section 48 of the transverse connector is inhibited. The drive tool 86 may be, but is not limited to, a diamond drive, a hex wrench, a star drive, a screwdriver, or a socket wrench. Preferably, the drive tool 86 for fastener 106 is the same instrument that may be used to rotate fastening systems 42 that couple the transverse connector 30 to elongated members 28. In alternate embodiments, tool openings 74 for cam systems 42 may have a different style than a tool opening for a fastener 106. For example, the tool openings 74 for the cam systems 42 may accept a diamond drive, while the tool opening 74 for the fastener 106 may be adapted to accept a drive head of a hex wrench.

Figure 18:
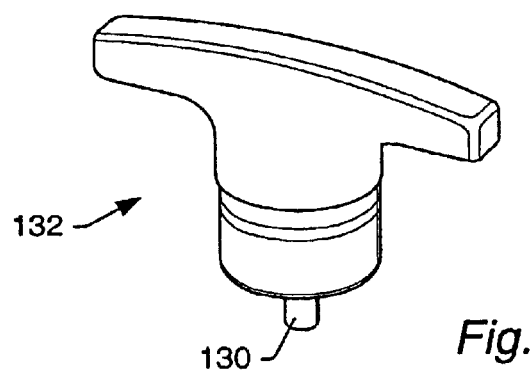
FIG. 18 is a perspective view of a torque wrench.

FIG. 14 shows an embodiment of a drive tool 86 that may be used to tighten a fastener 106 of a transverse connector 30". The handle 90 of the drive tool 86 may include an opening 128. The opening 128 may be configured to accept drive 130 of torque wrench 132. FIG. 18 shows an embodiment of a torque wrench 132. The torque wrench 132 may be used to inform a user when sufficient torque has been applied to the fastener 106. A sufficient amount of torque is enough torque to inhibit movement of a first section 46 of the transverse connector 30" relative to the second section 48 of the transverse connector.

In alternate transverse connector embodiments, an optional lining 104 may not be used. A fastener 106 may directly contact a shaft 108 of a first section 46 of a transverse connector 30" that is positioned through a holder 112 of a second section 48 of the transverse connector. The contact between the fastener 106, the shaft 108, and the holder 112 may inhibit movement of the first section 46 relative to the second section 48.

Figure 19:
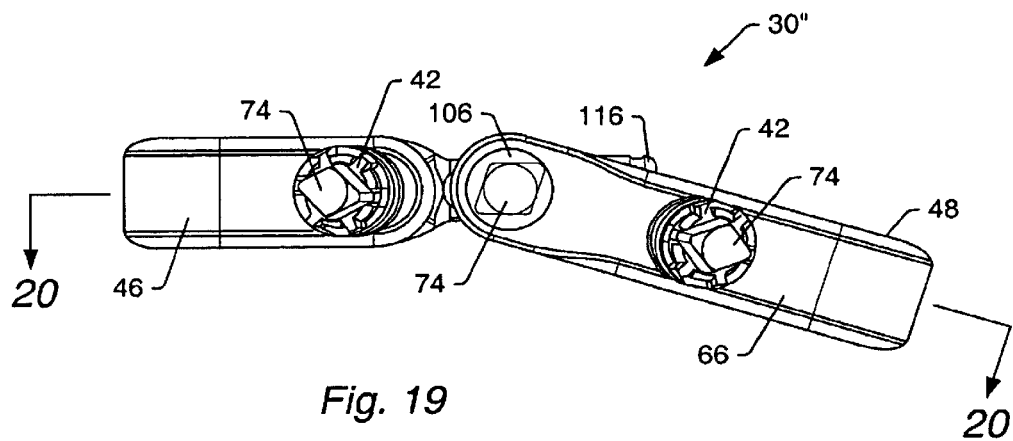
FIG. 19 is a top elevational view of an angulated adjustable transverse connector.

A second opening 122 in a holder 112 may allow a first section 46 to be angulated relative to a second section 48. FIG. 19 shows a top view of an embodiment of a transverse connector 30" where the first section 46 is angulated relative to the second section 48. Elongated members 28 of an orthopedic stabilization system 32 may be horizontally skewed relative to each other. The ability to angulate the first section 46 relative to the second section 48 allows the transverse connector 30" to be coupled to elongated members 28 that are horizontally skewed. In embodiments of stabilization systems 32, the elongated members may be horizontally parallel. To accommodate horizontally parallel elongated members 28, the first section 46 may be adjusted relative to the second section 48 so that there is no angulation between the first section and the second section.

Figure 22:
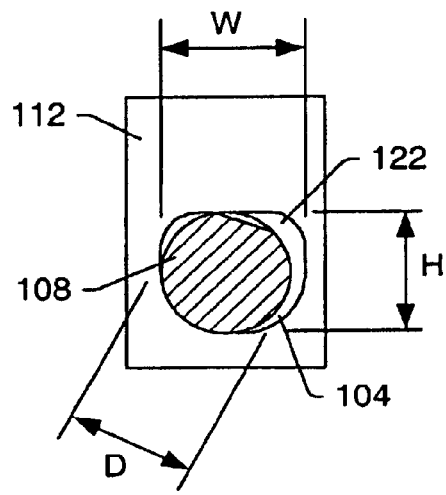
FIG. 22 is a cross sectional view of an adjustable transverse connector taken substantially along line 22—22 of FIG. 21.

To allow a first section 46 of a transverse connector 30" to be angulated relative to a second section 48 of the transverse connector, width W (as shown in FIG. 22) of a second opening 122 in a holder 112 of the second section may be larger than a diameter D of a shaft 108 passing through the holder. The large width W of the second opening 122 allows the shaft 108 to slide laterally within the second opening 122 until the fastener 106 is used to set the position of the shaft.

In an embodiment of a transverse connector 30", an angulation range of a first section 46 relative to a second section 48 may be from about 0° to about 18°. The amount of angulation may be less or greater than 18° in other embodiments. For example, in an embodiment, the angulation range of the first section 46 relative to the second section 48 is from 0° to 10°; and in another embodiment, the angulation range is from 0° to 30°. Larger or smaller ranges may also be used. A position of a second opening 122 may be altered to change the limits of the angulation. For example, in an embodiment, the second opening 122 is positioned so that the angulation range is from 10° to 30°. Other embodiments may allow for different amounts of angulation or for different angulation ranges. If the transverse connector 30" cannot be angulated in a desired direction when a first section 46 is placed on a first elongated member 28, the first section may be removed from the elongated member and placed on a second elongated member to allow the transverse connector to be angulated in the desired direction.

A second opening 122 in a holder 112 may allow a first section 46 of a transverse connector 30" to be rotated relative to a second section 48 of the transverse connector. Elongated members 28 of an orthopedic stabilization system 32 may be vertically parallel, or the elongated members may be vertically skewed relative to each other. If the elongated members 28 are vertically skewed relative to each other, the amount of skew is typically less than about 5°, but the skew may be as large as 20° or more. The ability to rotate the first section 46 of the transverse connector 30" allows the transverse connector to be coupled to vertically skewed elongated members 28.

Figure 21:
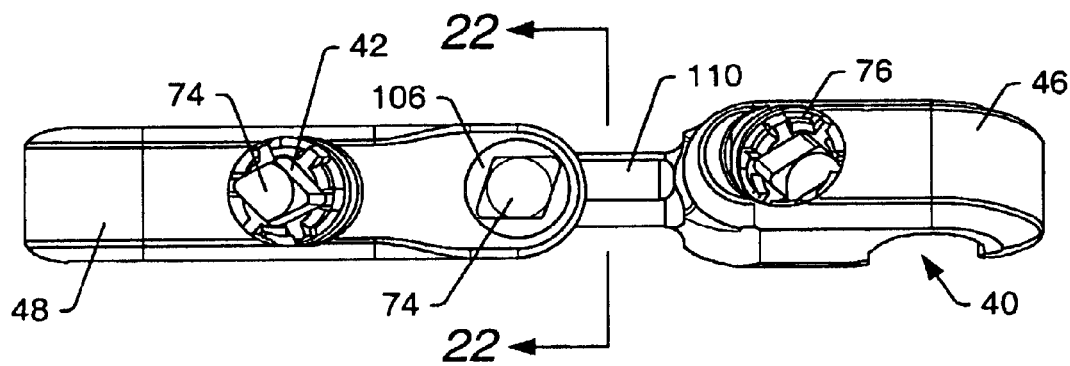
FIG. 21 is a top elevational view of a rotated adjustable transverse connector.

To allow a first section 46 of a transverse connector 30" to be rotated relative to a second section 48 of the transverse connector, a shaft 108 of the first section is allowed to rotate within a lining 104. In an embodiment, height H of a second opening 122 in the second section 48 is slightly larger than a diameter D of the shaft 108. The height H of the second opening 122 allows the shaft 108 to be rotated a full 360° relative to the second section 48. In an alternate embodiment, which is shown in FIG. 22, the height H of the second opening 122 is smaller than the diameter D of the shaft 108 of the first section 46. A flat surface 110 of the shaft 108 may limit the range of rotation of the first section 46 relative to the second section 48 to a useful range. If a user tries to rotate the first section 46 beyond a limited range, an edge of the flat surface 110 will contact the holder 112 and inhibit rotation of the first section 46 relative to the second section 48. The flat surface 110 of the shaft 108 and the second opening 122 may allow the first section 46 to rotate relative to the second section 48 about plus or minus 45° (for less than a 90° range of motion), preferably less than plus or minus 20° (for less than a 40° range of motion), and most preferably less than about plus or minus 10° (for less than a 20° range of motion). FIG. 21 shows an embodiment of a transverse connector 30" with a first section 46 that is rotated relative to a second section 48.

Limiting the range of rotational motion of the first section 46 relative to the second section 48 may inhibit the rotation of the first section into unusable positions. Unusable positions of the first section 46 relative to the second section 48 are positions that do not allow for easy instrument access to tool openings 74 of the transverse connector 30". For example, an embodiment of a transverse connector 30" may allow the first section 46 to rotate 360° relative to the second section 48. When the first section 46 is rotated 180° relative to the second section 48, the elongated member opening 40 of one of the sections will be oriented upwards, while the elongated member opening of the other section will be oriented downwards. The tool opening 74 of a cam system 42 that fastens the section with the upwards facing elongated member opening 40 to an elongated member 28 will not be easily accessible, and therefore, the transverse connector 30 is in an unusable position. Limiting the range of rotational motion of the first section 46 relative to the second section 48 may allow for easy instrument access to all parts of the transverse connector 30 that need to be tightened without excessive manipulation of the transverse connector.

Elongated member openings 40 of a transverse connector 30 may be placed over elongated members 28 of an orthopedic stabilization system 32. Cam systems 42 may be used to fasten the transverse connector 30 to the elongated members 28. A cam system 42 may be positioned within a cam system opening 60 in each section 46, 48 of the transverse connector 30. FIG. 20 shows a cross sectional view of an embodiment of a transverse connector 30". The sections 46, 48 of the transverse connector 30" may include cam system openings 60 for cam systems 42 (only one cam system is shown in FIG. 20). The cam systems 42 and cam system openings 60 for an adjustable transverse connector 30" may be the same as the cam systems and cam system openings for a fixed length transverse connector 30'. FIG. 13 shows an embodiment of a cam system 42.

Figure 23:
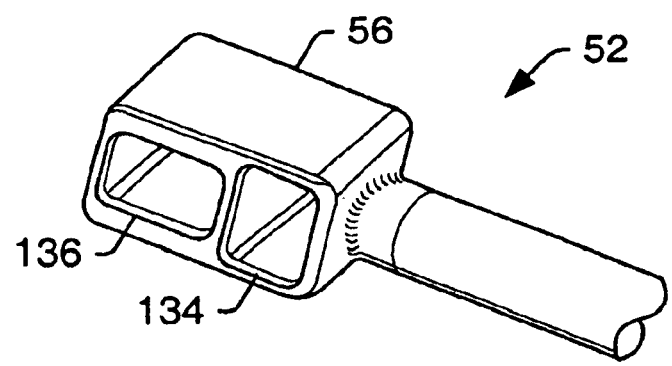
FIG. 23 shows a perspective view of an embodiment of a head of a bender that has two pockets.
Figure 24:
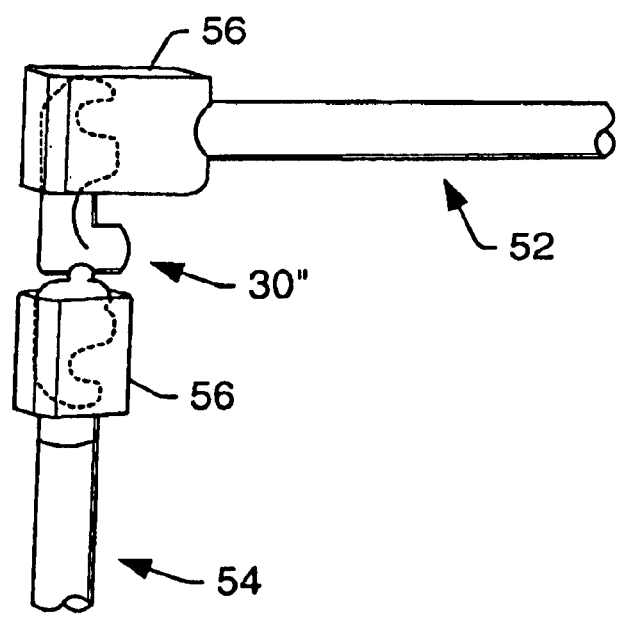
FIG. 24 shows a perspective view of the embodiment of the head of the bender shown in FIG. 23 engaged to an adjustable transverse connector.

FIG. 23 shows an embodiment of a head 56 of a bender 52. The head 56 may include two pockets 134 and 136. The first pocket 134 may be used to bend a fixed length transverse connector 30'. The second pocket 136 may be used to bend an adjustable transverse connector 30". FIG. 24 shows an adjustable transverse connector 30" positioned within benders 52, 54. The benders 52, 54 may be used to "tent" the transverse connector 30" so that a middle portion of the transverse connector is the highest portion of the transverse connector when the transverse connector is installed in a patient.

To form a transverse connector 30", a first section 46, a second section 48, and a lining 104 are machined. Cam systems 42 are also machined. The elongated member opening surfaces 50 and/or the contact surfaces of the engagers 68 may be textured so that the coefficient of friction between the surfaces and elongated members 28 placed against the surfaces will be high. Cam systems 42 are inserted into cam system openings 60 of the first section 46 and the second section 48. The cam systems 42 are inserted into the cam system openings 60 until the surfaces 82 of the cam systems 62 pass the shoulders 62 of the openings. A lining 104 is placed within a holder 112 of the second section 48. A shaft 108 of the first section 46 is inserted through the holder 112 and lining 104. End 116 of the shaft 108 is peened or flared to inhibit removal of the first section 46 from the second section 48. A fastener 106 is coupled to the holder 112.

Figure 25:
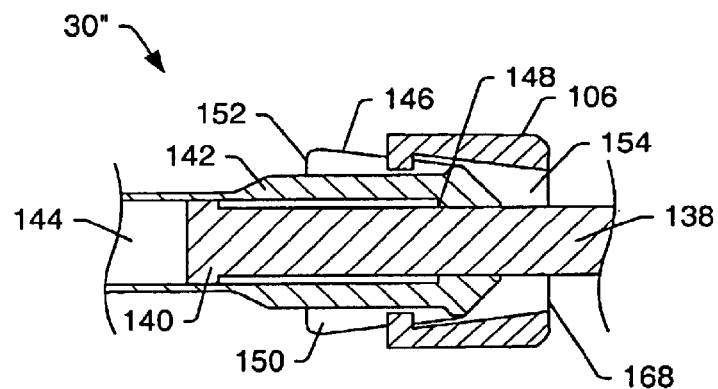
FIG. 25 shows a cross sectional view of a portion of the adjustable transverse connector shown in FIG. 7.

FIG. 7 shows an alternate embodiment of an adjustable transverse connector 30". The transverse connector 30" may include first section 46, second section 48, and fastener 106. FIG. 25 shows a cross sectional view of a portion of the transverse connector 30". The first section 46 may include shaft 138. The shaft 138 may include flared end 140. The second section 48 may include tapered collet 142 and hollow shaft 144. The fastener 106 may be a collar that is compression locked to the collet 142. The collet 142 may include holding members 146, ledge 148, longitudinal slots 150 and shoulder 152. The collar 106 may include a tapered bore 154 and tabs 156. The taper of the bore 154 may substantially correspond to the taper of the tapered collet 142. A maximum diameter of the collet 142 may be greater than a maximum diameter of the bore 154 of the collar 106. The tabs 156 may be placed within the longitudinal slots 150 in the collet 142 to couple the collar 106 to the second section 48. The tabs 156 and the diameter of the bore 154 relative to the diameter of the collet 142 may limit the axial range of motion of the collar 106 relative to the second section 48. The shaft 138 of the first section 46 may be inserted into the hollow shaft 144 of the second section 48. The flared end 140 of the shaft 138 may contact the ledge 148 of the collet 142 to inhibit the first section 46 from being separated from the second section 48.

A length of an adjustable transverse connector 30" shown in FIG. 7 may be adjusted by sliding a first section 46 axially relative to a second section 48. Also, the first section 46 may be rotated relative to the second section 48. The ability to rotate the first section 46 relative to the second section 48 allows the transverse connector 30" to be used with elongated members 28 that are skewed relative to each other such that the elongated members are not vertically parallel. When a desired length and rotation of the transverse connector 30" is established, the position of the first and second sections 46, 48 may be fixed to inhibit movement of the first section relative to the second section.

A portion of the shaft 138 may include a flat surface. An insert positioned and fixed within the hollow shaft 144 may limit the range of rotational motion of the first section 46 within the second section 48. An edge of the flat surface of the shaft 138 may contact an edge of the insert to limit the rotational range of the first section 46. Without an insert, the shaft may be able to rotate 360° within the hollow shaft. An insert within the hollow shaft 144 may allow the first section 46 to rotate relative to the second section 48 about plus or minus 45°, preferably less than plus or minus 20°, and most preferably less than about plus or minus 10°.

Figure 26:
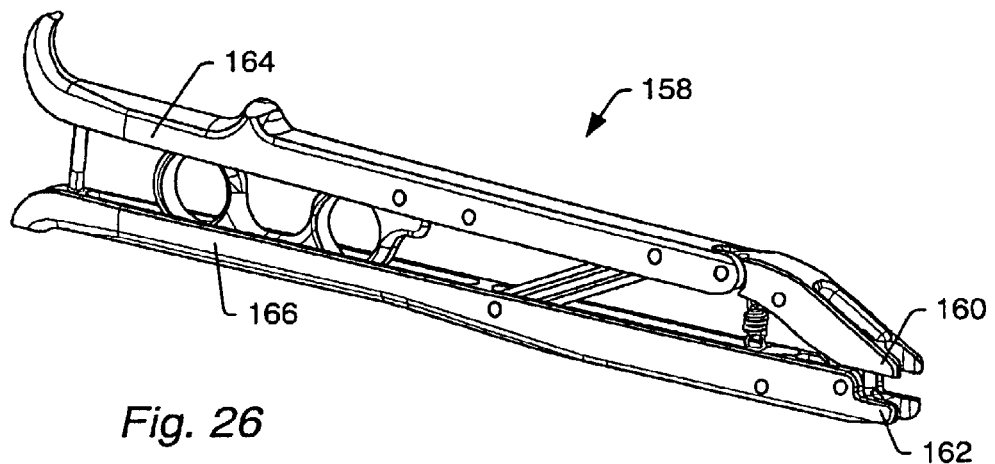
FIG. 26 is a perspective view of an instrument used to inhibit movement of a first section of a transverse connector relative to a second section of the transverse connector when the transverse connector has a collet and collar fastening system.

FIG. 26 shows an embodiment of a locking instrument 158 that may be used to fix a position of a first section 46 of a transverse connector 30" relative to a second section 48. The locking instrument 158 may include first jaw 160, second jaw 162, first handle 164, and 25 second handle 166. The first jaw 160 may be abutted against a shoulder 152 of a collet 142. The second jaw 162 may be abutted against front end 168 of the collar 106. Squeezing the handles 164, 166 together forces the collar 106 onto the collet 142 and compress the holding members 146 of the collet against the shaft 138 of the first section 46. Enough force may be applied to the collar 106 to frictionally lock the collar to the collet 142.

An outer surface of the shaft 138 and/or an inner surface of the holding members 146 may be roughened to increase the coefficient of friction between the first section 46 and the second section 48. Also, the inner surface of the collar 106 and/or the outer surface of the collet 142 may be roughened to increase the coefficient of friction between the collar and the collet.

To establish a bone stabilization system 32 using an adjustable transverse connector 30", a pair of contoured elongated members 28, or a single elongated member that is bent and contoured to fit on adjacent sides of a bone 34 or bones that are to be stabilized, may be coupled to the bone or bones being stabilized. The elongated members 28 may be coupled to the bone 34 or bones by fixation elements 36, as shown in FIG. 3. If necessary or desired, the transverse connector 30" may be bent using a pair of benders 52, 54 so that a middle portion of the transverse connector will be the highest part of the transverse connector when the transverse connector is installed in a patient. A first section 46 and a second section 48 of the transverse connector 30" may be placed over the elongated members 28 so that the elongated members are positioned within elongated member openings 40 of the transverse connector 30 at a desired location. The length, angulation, and rotation of the transverse connector 30" may be adjusted so that the elongated members 28 are positioned within the elongated member openings 40 with a large contact area between the elongated member opening surfaces 50 and the elongated members. A torque limiting wrench 94 may be placed on the transverse connector 30, and a shaft 92 of a drive tool 86 may be inserted through the hollow shaft 96 of the torque limiting wrench. A head 88 of a drive tool 86 may be inserted into a tool opening 74 of a first cam system 42 of the transverse connector 30. The drive tool 86 may be rotated to rotate the cam system 42 while applying counter torque with the torque limiting wrench 94. Rotating the cam system 42 may extend a cam 70 into an elongated member opening 40 so that the cam presses the elongated member 28 against the surface 50 of the elongated member opening. The drive tool 86 may be removed from the tool opening 74 of the first cam system 42.

The drive tool 86 and torque limiting wrench 94 may be repositioned so that the torque limiting wrench engages the transverse connector 30 and the head 88 of the drive tool 86 is inserted into the tool opening 74 of the second cam system 42. The drive tool 86 may be rotated, while applying counter torque with the torque limiting wrench 94, to force a cam 70 against the second elongated member 28 so that the cam presses the second elongated member against the second elongated member opening surface 50.

The torque limiting wrench 94 and the drive tool 86 may be repositioned so that the torque limiting wrench engages the transverse connector 30 and the head 88 of the drive tool is inserted into the tool opening 74 of the fastener 106. The fastener 106 may be tightened. A torque wrench 132 may be inserted into the opening 128 of the handle 90. The torque wrench 132 may be used to tighten the fastener 106 while counter torque is applied with the torque limiting wrench 94. Other transverse connectors 30 may be attached to the elongated members 28 at other locations along the lengths of the elongated members.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently referred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A connector for a bone stabilization system, comprising:
    a first section comprising an opening, a cam system in communication with the opening, and a connecting member, wherein the opening is configured to hold an elongated member and wherein the cam system is configured to couple the elongated member to the first section by extending an engager into the opening;
    a second section comprising a holder adapted to hold a portion of the connecting member and allow movement of the holder and connecting member relative to each other;
    a liner between the holder and the connecting member; and
    a fastener configured to inhibit movement of the connecting member and the holder relative to each other when in a first position, wherein the fastener in a second position allows the connecting member and the holder to be moved relative to each other.

2. The connector of claim 1, wherein a portion of the cam system comprises roughening.

3. The connector of claim 1, wherein the cam system is inhibited from being removed from the first section.

4. The connector of claim 1, wherein a rotational range of motion of the cam system is limited.

5. The connector of claim 4, wherein the rotational range of motion is limited to less than about 360°.

6. The connector of claim 4, wherein the rotational range of motion is limited to less than about 180°.

7. The connector of claim 4, wherein the rotational range of motion is limited to less than about 90°.

8. The connector of claim 1, further comprising a vibrational indicator that informs a user that the cam system is engaged.

9. The connector of claim 1, further comprising a visual indicator that informs a user that the cam system is engaged.

10. The connector of claim 9, further comprising a drive tool that activates the cam system, and wherein the visual indicator is a position of a handle of the drive tool relative to a position of the elongated member.

11. The connector of claim 1, wherein the second section further comprises an opening and a second cam system, wherein the second cam system is configured to extend an engager into the opening of the second section to secure the second section to a second elongated member positioned in the opening of the second section, wherein a distance between a surface of the opening of the first section and a surface of the opening of the second section is adjustable, and wherein the fastener inhibits adjustment of the distance during use.

12. The connector of claim 1, wherein the fastener comprises a setscrew.

13. The connector of claim 1, wherein the fastener in the second position allows rotation of a portion of the first section and a portion of the second section relative to each other.

14. The connector of claim 13, wherein a range of rotation of the portion of the first section relative to the portion of the second section is less than about 90°.

15. The connector of claim 1, wherein the fastener in the second position allows for angulation of a portion of the first section and a portion of the second section relative to each other.

16. The connector of claim 15, wherein a range of angulation of the portion of the first section and the portion of the second section relative to each other is less than about 30°.

17. The connector of claim 16, wherein a lower limit of the range of angulation of the portion of the first section and the portion of the second section relative to each other is about 0°.

18. The connector of claim 16, wherein a lower limit of the range of angulation of the portion of the first section and the portion of the second section relative to each other is greater than 0°.

* * * * *